United States Patent
Sidorenko et al.

(10) Patent No.: US 11,225,670 B2
(45) Date of Patent: Jan. 18, 2022

(54) PLANT PROMOTER FOR TRANSGENE EXPRESSION

(71) Applicants: CORTEVA AGRISCIENCE LLC, Indianapolis, IN (US); PIONEER HI-BRED INTERNATIONAL, INC., Johnston, IA (US)

(72) Inventors: Lyudmila Sidorenko, Johnston, IA (US); Cory M. Larsen, Zionsville, IN (US); Geny Anthony, Urbandale, IA (US); Shreedharan Sriram, Waukee, IA (US); Holly Jean Butler, Indianapolis, IN (US); Lynne E. Sims, Polk City, IA (US); Scott H. Diehn, Altoona, IA (US); Gilda M. Rauscher, Johnston, IA (US); Kevin G. Ripp, Johnston, IA (US); Knut Meyer, Colona, IL (US)

(73) Assignees: Corteva Agriscience LLC, Indianapolis, IN (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 16/758,649

(22) PCT Filed: Oct. 29, 2018

(86) PCT No.: PCT/US2018/057904
§ 371 (c)(1),
(2) Date: Apr. 23, 2020

(87) PCT Pub. No.: WO2019/089402
PCT Pub. Date: May 9, 2019

(65) Prior Publication Data
US 2020/0347395 A1    Nov. 5, 2020

Related U.S. Application Data

(60) Provisional application No. 62/727,007, filed on Sep. 5, 2018, provisional application No. 62/578,658, filed on Oct. 30, 2017.

(51) Int. Cl.
C12N 15/82    (2006.01)

(52) U.S. Cl.
CPC ..... *C12N 15/8223* (2013.01); *C12N 15/8216* (2013.01); *Y02A 40/146* (2018.01)

(58) Field of Classification Search
None
See application file for complete search history.

(56) References Cited

U.S. PATENT DOCUMENTS

2015/0329869 A1    11/2015  Venter
2020/0407742 A1*   12/2020  Sidorenka et al. ..... C12N 15/82

FOREIGN PATENT DOCUMENTS

WO    WO2007/065878 A2    6/2007

OTHER PUBLICATIONS

Walling, L et al; Nucleic Acids Research, No. 1 Jan. 1, 1988.
Mitra A, Hong K C, Gynheung A. "Structural and functional analyses of *Arabidopsis thaliana* chlorophyll a/b-binding protein (cab) promoters." Plant molecular biology 12.2 (1989): 169-179.
Liu, X, et al. "Identification and functional characterization of bidirectional gene pairs and their intergenic regions in maize." BMC genomics 15.1 (2014): 1-14.
Anderson S, and Kay S. "Functional dissection of circadian clock- and phytochrome-regulated transcription of the *Arabidopsis* CAB2 gene." Proceedings of the National Academy of Sciences 92.5 (1995): 1500-1504.
International Search Report for 18 873 873.6 dated Jul. 16, 2021.

* cited by examiner

*Primary Examiner* — Russell T Boggs

(57) ABSTRACT

This disclosure concerns compositions and methods for promoting transcription of a nucleotide sequence in a plant or plant cell, employing a promoter from a GmCAB2 gene. Some embodiments relate to a promoter or a 5' UTR from a GmCAB2 gene that functions in plants to promote transcription of operably linked nucleotide sequences. Other embodiments relate to a 3' UTR or a terminator from a GmCAB2 gene that functions in plants to promote transcription of operably linked nucleotide sequences.

19 Claims, 5 Drawing Sheets
Specification includes a Sequence Listing.

FIG.3A:

```
                          1                                                50
SEQ ID NO:2     (1)   --------------------------------------------------
SEQ ID NO:29    (1)   AGCAGATGAAGATAAAGAAAATGAAAAGATAAACTAAATTAGTCTAGAAT
SEQ ID NO:28    (1)   -GCAGATGAAGATAAAGAAAATGAAAAGATAAACTAAATTAGTCTAGAAT
                          51                                              100
SEQ ID NO:2     (1)   ------------------------------CAAATTCAAACAAACTTACATC
SEQ ID NO:29    (51)  TGTAGGCTAAAATAGAGTCGATTAGAGTACAAATTCAAACAAACTTACATC
SEQ ID NO:28    (50)  TGTAGGCTAAAATAGAGTCGATTAGAGTACAAATTCAAACAAACTTACATC
                          101                                             150
SEQ ID NO:2     (23)  CCCCGAAAGCTTTCAAGTAAGCCGAAGTGACCTATTAGCTTCGTTTTTCA
SEQ ID NO:29    (101) CCCCGAAAGCTTTCAAGTAAGCCGAAGTGACCTATTAGCTTCGTTTTTCA
SEQ ID NO:28    (100) CCCCGAAAGCTTTCAAGTAAGCCGAAGTGACCTATTAGCTTCGTTTTTCA
                          151                                             200
SEQ ID NO:2     (73)  TGCTTCCATGATTAAAAAAGTAATTGCAGAACTCCTTCCAGTATATGAGC
SEQ ID NO:29    (151) TGCTTCCATGATTAAAAAAGTAATTGCAGAACTCCTTCCAGTATATGAGC
SEQ ID NO:28    (150) TGCTTCCATGATTAAAAAAGTAATTGCAGAACTCCTTCCAGTATATGAGC
                          201                                             250
SEQ ID NO:2     (123) TCGAATGGGGTGCCAGATATGCTAATTAATTACTTTTATGATGCAGGCA
SEQ ID NO:29    (201) TCGAATGGGGTGCCAGATATGCTAATTAATTACTTTTATGATGCAGGCA
SEQ ID NO:28    (200) TCGAATGGGGTGCCAGATATGCTAATTAATTACTTTTATGATGCAGGCA
                          251                                             300
SEQ ID NO:2     (173) AGTGTGTTTTCAGATGCTGTTCGGGATGATGTTGATTTTATAAGTATGA
SEQ ID NO:29    (251) AGTGTGTTTTCAGATGCTGTTCGGGATGATGTTGATTTTATAAGTATGA
SEQ ID NO:28    (250) AGTGTGTTTTCAGATGCTGTTCGGGATGATGTTGATTTTATAAGTATGA
                          301                                             350
SEQ ID NO:2     (223) ACTGCACTCCTTTAGCTTTGAAGTTTGATCACTAGTGGATAAATTATTTA
SEQ ID NO:29    (301) ACTGCACTCCTTTAGCTTTGAAGTTTGATCACTAGTGGATAAATTATTTA
SEQ ID NO:28    (300) ACTGCACTCCTTTAGCTTTGAAGTTTGATCACTAGTGGATAAATTATTTA
                          351                                             400
SEQ ID NO:2     (273) TATCTTGAGCTTTGAAAATCTTCCAATGAAACTTCATTCACACTTTCTGT
SEQ ID NO:29    (351) TATCTTGAGCTTTGAAAATCTTCCAATGAAACTTCATTCACACTTTCTGT
SEQ ID NO:28    (350) TATCTTGAGCTTTGAAAATCTTCCAATGAAACTTCATTCACACTTTCTGT
                          401                                             450
SEQ ID NO:2     (323) GAAAAATATCATCTATTAAAGAATCTTGTCGTGGTCAATGCTATGCATGA
SEQ ID NO:29    (401) GAAAAATATCATCTATTAAAGAATCTTGTCGTGGTCAATGCTATGCATGA
SEQ ID NO:28    (400) GAAAAATATCATCTATTAAAGAATCTTGTCGTGGTCAATGCTATGCATGA
                          451                                             500
SEQ ID NO:2     (373) CAACATATTAACTATTTAAAAGATAACTTAAAATTATAAATAGTTACATA
SEQ ID NO:29    (451) CAACATATTAACTATTTAAAAGATAACTTAAAATTATAAATAGTTACATA
SEQ ID NO:28    (450) CAACATATTAACTATTTAAAAGATAACTTAAAATTATAAATAGTTACATA
                          501                                             550
SEQ ID NO:2     (423) TTATAAAATGCTGTGGTGGACATGTTACCACTTGTAGAATTTATATAGTA
SEQ ID NO:29    (501) TTATAAAATGCTGTGGTGGACATGTTACCACTTGTAGAATTTATATAGTA
SEQ ID NO:28    (500) TTATAAAATGCTGTGGTGGACATGTTACCACTTGTAGAATTTATATAGTA
                          551                                             600
SEQ ID NO:2     (473) AAATTGAATCTATAACAACACGACACTTTATGTTTATGGAATTGTCATGT
SEQ ID NO:29    (551) AAATTGAATCTATAACAACACGACACTTTATGTTTATGGAATTGTCATGT
SEQ ID NO:28    (550) AAATTGAATCTATAACAACACGACACTTTATGTTTATGGAATTGTCATGT
                          601                                             650
SEQ ID NO:2     (523) ATGTGATAATAAATAAGATTAATGAAATTATTATAAAAAACAAGGCCTTA
SEQ ID NO:29    (601) ATGTGATAATAAATAAGATTAATGAAATTATTATAAAAAACAAGGCCTTA
SEQ ID NO:28    (600) ATGTGATAATAAATAAGATTAATGAAATTATTATAAAAAACAAGGCCTTA
```

FIG.3B:

```
                         651                                                   700
SEQ ID NO:2     (573)    ATCGAAAATTCAATATCTTTCTATTTTTTTATTTTATAATAGTAATATAA
SEQ ID NO:29    (651)    ATCGAAAATTCAATATCTTTCTATTTTTTTATTTTATAATAGTAATATAA
SEQ ID NO:28    (650)    ATCGAAAATTCAATATCTTTCTATTTTTTTATTTTATAATAGTAATATAA
                         701                                                   750
SEQ ID NO:2     (623)    TTAAGGTGCTTTATTTTGTTTTCTCTTAATTACCGTAATTCTCATTTAAA
SEQ ID NO:29    (701)    TTAAGGTGCTTTATTTTGTTTTCTCTTAATTACCGTAATTCTCATTTAAA
SEQ ID NO:28    (700)    TTAAGGTGCTTTATTTTGTTTTCTCTTAATTACCGTAATTCTCATTTAAA
                         751                                                   800
SEQ ID NO:2     (673)    TACAACTTTTCTAGCTTATGATATTGAAAGTTAATTAAAAAACCAATAAC
SEQ ID NO:29    (751)    TACAACTTTTCTAGCTTATGATATTGAAAGTTAATTAAAAAACCAATAAC
SEQ ID NO:28    (750)    TACAACTTTTCTAGCTTATGATATTGAAAGTTAATTAAAAAACCAATAAC
                         801                                                   850
SEQ ID NO:2     (723)    GTCCTGAATTTTAATCTAAAACTTCTAGTACGTTTGGTTTCACATTTTAG
SEQ ID NO:29    (801)    GTCCTGAATTTTAATCTAAAACTTCTAGTACGTTTGGTTTCACATTTTAG
SEQ ID NO:28    (800)    GTCCTGAATTTTAATCTAAAACTTCTAGTACGTTTGGTTTCACATTTTAG
                         851                                                   900
SEQ ID NO:2     (773)    ATATAATTTTTAAAAGTTAATAGTTATAAATTTGTATTTTAAATGTGATT
SEQ ID NO:29    (851)    ATATAATTTTTAAAAGTTAATAGTTATAAATTTGTATTTTAAATGTGATT
SEQ ID NO:28    (850)    ATATAATTTTTAAAAGTTAATAGTTATAAATTTGTATTTTAAATGTGATT
                         901                                                   950
SEQ ID NO:2     (823)    TTTTTCTATTTTAATGACTTTTAACCATGTACAGTTATTCATACTGA
SEQ ID NO:29    (901)    TTTTTCTATTTTAATGACTTTTAACCATGTACAGTTATTCATACTGA
SEQ ID NO:28    (900)    TTTTTCTATTTTAATGACTTTTAACCATGTACAGTTATTCATACTGA
                         951                                                  1000
SEQ ID NO:2     (873)    TTTTTAAACTGTTTGCTTGAAGAGACGGTTTTTGACACCAAGTTAAAGA
SEQ ID NO:29    (951)    TTTTTAAACTGTTTGCTTGAAGAGACGGTTTTTGACACCAAGTTAAAGA
SEQ ID NO:28    (950)    TTTTTAAACTGTTTGCTTGAAGAGACGGTTTTTGACACCAAGTTAAAGA
                         1001                                                 1050
SEQ ID NO:2     (923)    GGTCATTATCTCTTCTAAAATCCTAAGATATAATTTCCAAATGAAACCAA
SEQ ID NO:29    (1001)   GGTCATTATCTCTTCTAAAATCCTAAGATATAATTTCCAAATGAAACCAA
SEQ ID NO:28    (1000)   GGTCATTATCTCTTCTAAAATCCTAAGATATAATTTCCAAATGAAACCAA
                         1051                                                 1100
SEQ ID NO:2     (973)    ATTTGTAATGTAGCGAAGATGAGCTGCCACATTGTGTTCTTGAGGTCGAG
SEQ ID NO:29    (1051)   ATTTGTAATGTAGCGAAGATGAGCTGCCACATTGTGTTCTTGAGGTCGAG
SEQ ID NO:28    (1050)   ATTTGTAATGTAGCGAAGATGAGCTGCCACATTGTGTTCTTGAGGTCGAG
                         1101                                                 1150
SEQ ID NO:2     (1023)   GCACTACTAGCCCTGTGTTTCTGTGTAGTTTTACTAGCAACACAAGTTTT
SEQ ID NO:29    (1101)   GCACTACTAGCCCTGTGTTTCTGTGTAGTTTTACTAGCAACACAAGTTTT
SEQ ID NO:28    (1100)   GCACTACTAGCCCTGTGTTTCTGTGTAGTTTTACTAGCAACACAAGTTTT
                         1151                                                 1200
SEQ ID NO:2     (1073)   TTCTTTTTTTCAAAAATAAAAAAGAAAGAAGAAAAAAAATGTGATGGGTC
SEQ ID NO:29    (1151)   TTCTTTTTTTCAAAAATAAAAAAGAAAGAAGAAAAAAAATGTGATGGGTC
SEQ ID NO:28    (1150)   TTCTTTTTTTCAAAAATAAAAAAGAAAGAAGAAAAAAAATGTGATGGGTC
                         1201                                                 1250
SEQ ID NO:2     (1123)   ACTCACGGGTTGCAATGTTAGTGTAGCATCAGCCCAATCCAAACTATCT
SEQ ID NO:29    (1201)   ACTCACGGGTTGCAATGTTAGTGTAGCATCAGCCCAATCCAAACTATCT
SEQ ID NO:28    (1200)   ACTCACGGGTTGCAATGTTAGTGTAGCATCAGCCCAATCCAAACTATCT
                         1251                                                 1300
SEQ ID NO:2     (1173)   TCCATACCAATTTCCAAGTTTTAATTTAAATTTAAATTTCTTGACTCTGT
SEQ ID NO:29    (1251)   TCCATACCAATTTCCAAGTTTTAATTTAAATTTAAATTTCTTGACTCTGT
SEQ ID NO:28    (1250)   TCCATACCAATTTCCAAGTTTTAATTTAAATTTAAATTTCTTGACTCTGT
```

FIG.3C:

```
                      1301                                              1350
SEQ ID NO:2  (1223)   TGGACCTGAATTGTGTGGCTTACATTGACCCTCTCGAAAACATCTGAGGA
SEQ ID NO:29 (1301)   TGGACCTGAATTGTGTGGCTTACATTGACCCTCTCGAAAACATCTGAGGA
SEQ ID NO:28 (1300)   TGGACCTGAATTGTGTGGCTTACATTGACCCTCTCGAAAACATCTGAGGA
                      1351                                              1400
SEQ ID NO:2  (1273)   AGAAGTCTTTGCATCCACGTGGCAGAATAAGAGCCACTATAGCATGACAA
SEQ ID NO:29 (1351)   AGAAGTCTTTGCATCCACGTGGCAGAATAAGAGCCACTATAGCATGACAA
SEQ ID NO:28 (1350)   AGAAGTCTTTGCATCCACGTGGCAGAATAAGAGCCACTATAGCATGACAA
                      1401                                              1450
SEQ ID NO:2  (1323)   AATATCAGCATGAGAATCCACATCCAAATCCACGACCAATGAGGTGTTGC
SEQ ID NO:29 (1401)   AATATCAGCATGAGAATCCACATCCAAATCCACGACCAATGAGGTGTTGC
SEQ ID NO:28 (1400)   AATATCAGCATGAGAATCCACATCCAAATCCACGACCAATGAGGTGTTGC
                      1451
SEQ ID NO:2  (1373)   TGAG
SEQ ID NO:29 (1451)   TGAG
SEQ ID NO:28 (1450)   TGAG
```

PLANT PROMOTER FOR TRANSGENE EXPRESSION

INCORPORATION BY REFERENCE

This application claims the benefit of U.S. Provisional Patent Application Ser. No. 62/578,658 filed Oct. 30, 2017 and U.S. Provisional Patent Application Ser. No. 62/727,007 filed Sep. 21, 2018, both of which are expressly incorporated by reference in their entirety herein.

Incorporated by reference in its entirety is a computer-readable nucleotide/amino acid sequence listing submitted concurrently herewith and identified as follows: one 32.4 KB ASCII (Text) file named "79351 [2] SEQ LISTING_ST25" created on Sep. 4, 2018.

BACKGROUND

Many plant species are capable of being transformed with transgenes to introduce agronomically desirable traits or characteristics. The resulting plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation results in transgenic plants that possess desirable traits and phenotypes. However, novel gene regulatory elements that allow the production of transgenic plant species to highly express multiple transgenes engineered as a trait stack are desirable.

Likewise, novel gene regulatory elements that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a promoter operably linked to: a polylinker sequence; a non-GmCAB2 heterologous coding sequence; wherein said promoter comprises a polynucleotide sequence that has at least 95% sequence identity with SEQ ID NO:2. In further embodiments, said promoter is 1,299 bp in length. In other embodiments, said promoter consists of a polynucleotide sequence that has at least 95% sequence identity with SEQ ID NO:2. In additional embodiments, said promoter is operably linked to a heterologous coding sequence. Accordingly, the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other embodiments, the nucleic acid vector comprises a terminator polynucleotide sequence. In additional embodiments, the nucleic acid vector comprises a 3' untranslated polynucleotide sequence. In additional embodiments, the nucleic acid vector comprises a 5' untranslated polynucleotide sequence. In additional embodiments, the nucleic acid vector comprises an intron sequence. In additional embodiments, said promoter has tissue preferred expression. In further embodiments, the nucleic acid vector comprises a polynucleotide sequence that has at least 95% sequence identity with SEQ ID NO:2 operably linked to a heterologous coding sequence. In further embodiments, said plant is selected from the group consisting of Zea mays, wheat, rice, sorghum, oats, rye, bananas, sugar cane, Glycine max, cotton, Arabidopsis, tobacco, sunflower, and canola. In yet another embedment, said plant is Glycine max. In some embodiments, the heterologous coding sequence is inserted into the genome of said plant. In other embodiments, the promoter comprises a polynucleotide sequence having at least 95% sequence identity with SEQ ID NO:2 and said promoter is operably linked to a heterologous coding sequence. In additional embodiments, the transgenic plant comprises a 3' untranslated sequence. In further embodiments, said heterologous coding sequence has tissue preferred expression. In additional embodiments, the transgenic plant comprises said promoter of 1,299 bp in length.

In embodiments of the subject disclosure, the disclosure relates to a method for producing a transgenic plant cell, the method comprising the steps of transforming a plant cell with a gene expression cassette comprising a GmCAB2 promoter operably linked to at least one polynucleotide sequence of interest; isolating the transformed plant cell comprising the gene expression cassette; and, producing a transgenic plant cell comprising the GmCAB2 promoter operably linked to at least one polynucleotide sequence of interest. In other embodiments, the transformation of a plant cell is performed with a plant transformation method. In some aspects, the plant transformation method is selected from the group consisting of an Agrobacterium-mediated transformation method, a biolistics transformation method, a silicon carbide transformation method, a protoplast transformation method, and a liposome transformation method. In further embodiments, the polynucleotide sequence of interest is expressed in a plant cell. In other embodiments, the polynucleotide sequence of interest is stably integrated into the genome of the transgenic plant cell. In further embodiments, the method comprises regenerating the transgenic plant cell into a transgenic plant; and, obtaining the transgenic plant, wherein the transgenic plant comprises the gene expression cassette comprising the GmCAB2 promoter operably linked to at least one polynucleotide sequence of interest. In other embodiments, the transgenic plant cell is a monocotyledonous transgenic plant cell or a dicotyledonous transgenic plant cell. Examples of a dicotyledonous transgenic plant cell includes an Arabidopsis plant cell, a tobacco plant cell, a Glycine max plant cell, a canola plant cell, and a cotton plant cell. Examples of a monocotyledonous transgenic plant cell includes a *Zea mays* plant cell, a rice plant cell, and a wheat plant cell. In some embodiments, the GmCAB2 promoter comprises the polynucleotide of SEQ ID NO:2. In other embodiments, the GmCAB2 promoter comprises a first polynucleotide sequence of interest operably linked to the 3' end of SEQ ID NO:2. In additional embodiments, the method comprises introducing into the plant cell a polynucleotide sequence of interest operably linked to a GmCAB2 promoter. In further embodiments, the polynucleotide sequence of interest operably linked to the GmCAB2 promoter is introduced into the plant cell by a plant transformation method. Examples of plant transformation methods include *Agrobacterium*-mediated transformation method, a biolistics transformation method, a silicon carbide transformation method, a protoplast transformation method, and a liposome transformation method. In further embodiments, the polynucleotide sequence of interest is expressed in embryonic cell tissue. In additional embodiments, the polynucleotide sequence of interest is stably integrated into the genome of the plant cell. In some embodiments, the transgenic plant cell is a monocotyledonous plant cell or a dicotyledonous plant cell. Examples of dicotyledonous plant cells include an *Arabidopsis* plant cell, a tobacco plant cell, a *Glycine max* plant cell, a canola plant cell, and a cotton plant cell. Examples of monocotyledonous plant cells include a *Zea mays* plant cell, a rice plant cell, and a wheat plant cell.

In embodiments of the subject disclosure, the disclosure relates to a transgenic plant cell comprising a GmCAB2 promoter. In other embodiments, the transgenic plant cell comprises a transgenic event. In further embodiments, the transgenic event comprises an agronomic trait. Examples of agronomic traits include an insecticidal resistance trait, herbicide tolerance trait, nitrogen use efficiency trait, water use efficiency trait, nutritional quality trait, DNA binding trait, selectable marker trait, small RNA trait, or any combination thereof. In further embodiments, the agronomic trait comprises an herbicide tolerant trait. In an aspect of this embodiment, the herbicide tolerant trait comprises an aad-1 coding sequence. In yet another embodiment, the transgenic plant cell produces a commodity product. Examples of a commodity product includes protein concentrate, protein isolate, grain, meal, flour, oil, or fiber. In further embodiments, the transgenic plant cell is selected from the group consisting of a dicotyledonous plant cell or a monocotyledonous plant cell. For example, the dicotyledonous plant cell is a *Glycine max* plant cell. In additional embodiments, the GmCAB2 promoter comprises a polynucleotide with at least 95% sequence identity to the polynucleotide of SEQ ID NO:2, SEQ ID NO:28, or SEQ ID NO:29. In other embodiments, the GmCAB2 promoter is 1,299 bp in length. In some embodiments, the GmCAB2 promoter consists of SEQ ID NO:2, SEQ ID NO:28, or SEQ ID NO:29. In subsequent embodiments, the GmCAB2 promoter comprises a first polynucleotide sequence of interest operably linked to the 3' end of SEQ ID NO:2. In other embodiments, the agronomic trait is expressed in plant tissues. In further embodiments, the isolated polynucleotide comprises a nucleic acid sequence with at least 95% sequence identity to the polynucleotide of SEQ ID NO:2, SEQ ID NO:28, or SEQ ID NO:29. In additional embodiments, the isolated polynucleotide drives tissue preferred expression. In other embodiments, the isolated polynucleotide comprises expression activity within a plant cell. In some embodiments, the isolated polynucleotide comprise an open-reading frame polynucleotide coding for a polypeptide; and a termination sequence. In subsequent embodiments, the polynucleotide of SEQ ID NO:2 is 1,299 bp in length. In subsequent embodiments, the polynucleotide of SEQ ID NO:28 is 1,453 bp in length. In subsequent embodiments, the polynucleotide of SEQ ID NO:29 is 1,454 bp in length.

In embodiments of the subject disclosure, the disclosure relates to a gene expression cassette comprising a promoter operably linked to a heterologous coding sequence, wherein the promoter comprises a polynucleotide comprising a sequence identity of at least 95% to SEQ ID NO:2, SEQ ID NO:28, or SEQ ID NO:29. In some embodiments, the polynucleotide has at least 95% sequence identity to SEQ ID NO:2, SEQ ID NO:28, or SEQ ID NO:29. In additional embodiments, the gene expression cassette comprises an intron. In further embodiments, the gene expression cassette comprises a 5' UTR. In subsequent embodiments, the promoter has tissue preferred expression. In other embodiments, the promoter is operably linked to a heterologous coding sequence that encodes a polypeptide or a small RNA gene. Examples of the encoded polypeptide or small RNA gene include a heterologous coding sequence conferring insecticidal resistance, herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker. In additional embodiments, the gene expression cassette comprises a 3' untranslated region. For example, the 3' untranslated region has at least 95% sequence identity to SEQ ID NO:4. In additional embodiments, the gene expression cassette comprises a 5' untranslated region. For example, the 5' untranslated region has at least 95% sequence identity to SEQ ID NO:3. In additional embodiments, the gene expression cassette comprises a terminator region. For example, the terminator region has at least 95% sequence identity to SEQ ID NO:5. In other embodiments the subject disclosure relates to a recombinant vector comprising the gene expression cassette, wherein the vector is selected from the group consisting of a plasmid, a cosmid, a bacterial artificial chromosome, a virus, and a bacteriophage. In other embodiments the subject disclosure relates to a transgenic cell comprising the gene expression cassette. In an aspect of this embodiment, the transgenic cell is a transgenic plant cell. In other aspects of this embodiment the transgenic plant comprises the transgenic plant cell. In further aspects the transgenic plant is a monocotyledonous plant or dicotyledonous plant. Examples of a monocotyledonous plant is include a maize plant, a rice plant, and a wheat plant. In further aspects of the embodiment, the transgenic plant produces a seed comprises the gene expression cassette. In other embodiments, the promoter is a tissue preferred promoter. In some embodiments, the tissue preferred promoter is a tissue preferred promoter.

In embodiments of the subject disclosure, the disclosure relates to a nucleic acid vector comprising a promoter operably linked to: a polylinker sequence; a non-GmCAB2 heterologous coding sequence; wherein said promoter comprises a polynucleotide sequence that has at least 95% sequence identity with SEQ ID NO:28. In further embodiments, said promoter is 1,453 bp in length. In other embodiments, said promoter consists of a polynucleotide sequence that has at least 95% sequence identity with SEQ ID NO:28. In additional embodiments, said promoter is operably linked to a heterologous coding sequence. Accordingly, the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other embodiments, the nucleic acid vector comprises a terminator polynucleotide sequence. In additional embodiments, the nucleic acid vector comprises a 3' untranslated polynucleotide sequence. In additional embodiments, the nucleic acid vector comprises a 5' untranslated polynucleotide sequence. In additional embodiments, the nucleic acid vector comprises an intron sequence. In additional embodiments, said promoter has tissue preferred expression. In further embodiments, the nucleic acid vector comprises a polynucleotide sequence that has at least 95% sequence identity with SEQ ID NO:28 operably linked to a heterologous coding sequence. In further embodiments, said plant is selected from the group consisting of Zea mays, wheat, rice, sorghum, oats, rye, bananas, sugar cane, Glycine max, cotton, Arabidopsis, tobacco, sunflower, and canola. In yet another embedment, said plant is Glycine max. In some embodiments, the heterologous coding sequence is inserted into the genome of said plant. In other embodiments, the promoter comprises a polynucleotide sequence having at least 95% sequence identity with SEQ ID NO:28 and said promoter is operably linked to a heterologous coding sequence. In additional embodiments, the transgenic plant comprises a 3' untranslated sequence. In further embodiments, said heterologous coding sequence has tissue preferred expression. In additional embodiments, the transgenic plant comprises said promoter of 1,453 bp in length.

In embodiments of the subject disclosure, the disclosure relates to a nucleic acid vector comprising a promoter operably linked to: a polylinker sequence; a non-GmCAB2 heterologous coding sequence; wherein said promoter comprises a polynucleotide sequence that has at least 95% sequence identity with SEQ ID NO:29. In further embodiments, said promoter is 1,454 bp in length. In other embodiments, said promoter consists of a polynucleotide sequence that has at least 95% sequence identity with SEQ ID NO:29. In additional embodiments, said promoter is operably linked to a heterologous coding sequence. Accordingly, the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other embodiments, the nucleic acid vector comprises a terminator polynucleotide sequence. In additional embodiments, the nucleic acid vector comprises a 3' untranslated polynucleotide sequence. In additional embodiments, the nucleic acid vector comprises a 5' untranslated polynucleotide sequence. In additional embodiments, the nucleic acid vector comprises an intron sequence. In additional embodiments, said promoter has tissue preferred expression. In further embodiments, the nucleic acid vector comprises a polynucleotide sequence that has at least 95% sequence identity with SEQ ID NO:29 operably linked to a heterologous coding sequence. In further embodiments, said plant is selected from the group consisting of Zea mays, wheat, rice, sorghum, oats, rye, bananas, sugar cane, Glycine max, cotton, Arabidopsis, tobacco, sunflower, and canola. In yet another embedment, said plant is Glycine max. In some embodiments, the heterologous coding sequence is inserted into the genome of said plant. In other embodiments, the promoter comprises a polynucleotide sequence having at least 95% sequence identity with SEQ ID NO:29 and said promoter is operably linked to a heterologous coding sequence. In additional embodiments, the transgenic plant comprises a 3' untranslated sequence. In further embodiments, said heterologous coding sequence has tissue preferred expression. In additional embodiments, the transgenic plant comprises said promoter of 1,454 bp in length.

The foregoing and other features will become more apparent from the following detailed description of several embodiments, which proceeds with reference to the accompanying figures.

BRIEF DESCRIPTION OF THE FIGURES

FIG. 3A, FIG. 3B, and FIG. 3C Provides an alignment of SEQ ID NO:2, SEQ ID NO:28, and SEQ ID NO:29 using the AlignX global alignment program from the Vector NTI Advance 11.0 bioinformatic computer program that is available from Invitrogen Corporation. SEQ ID NO:28 and SEQ ID NO:29 share 99.9% sequence identity. SEQ ID NO:2 and SEQ ID NO:28 share 94.5% sequence identity. SEQ ID NO:2 and SEQ ID NO:29 share 94.4% sequence identity.

DETAILED DESCRIPTION

I. Overview of Several Embodiments

Figure 1:
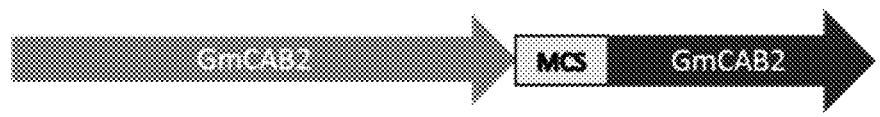
FIG. 1. Provides a figure of a linear synthetic DNA fragment containing GmCAB2 promoter, 5' UTR and terminator linked by the multiple cloning site and franked by Gateway aatL1 and aatL2 recombination sites.

Development of transgenic plant products is becoming increasingly complex. Commercially viable transgenic plants now require the stacking of multiple transgenes into a single locus. Plant promoters and 3' UTRs/terminators used for basic research or biotechnological applications are generally unidirectional, directing only one gene that has been fused at its 3' end (downstream) for the promoter, or at its 5' end (upstream) for the 3' U1R/terminator. Accordingly, each transgene/heterologous coding sequence usually requires a promoter and 3' UTR/terminator for expression, wherein multiple regulatory elements are required to express multiple transgenes within one gene stack. With an increasing number of transgenes in gene stacks, the same promoter and/or 3' UTR/terminator is routinely used to obtain optimal levels of expression patterns of different transgenes. Obtaining optimal levels of transgene/heterologous coding sequence expression is necessary for the production of a single polygenic trait. Unfortunately, multi-gene constructs driven by the same promoter and/or 3' UTR/terminator are known to cause gene silencing resulting in less efficacious transgenic products in the field. The repeated promoter and/or 3' UTR/terminator elements may lead to homology-based gene silencing. In addition, repetitive sequences within a transgene/heterologous coding sequence may lead to gene intra locus homologous recombination resulting in polynucleotide rearrangements. The silencing and rearrangement of transgenes will likely have an undesirable affect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters and/or 3' UTRs/terminators are required to develop transgenic crops that drive the expression of multiple genes.

A particular problem in promoter and/or 3' UTR/terminator identification is the need to identify tissue-specific/preferred promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters and/or 3' UTRs/terminators can be initially identified from observing the expression of genes, which are expressed in particular tissues or at particular time periods during plant development. These tissue specific/preferred promoters and/or 3' UTRs/terminators are required for certain applications in the transgenic plant industry and are desirable as they permit specific expression of heterologous genes in a tissue and/or developmental stage selective manner, indicating expression of the heterologous gene differentially at various organs, tissues and/or times, but not in other undesirable tissues. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene/heterologous coding sequence in plant tissues that are in a particular growth or developmental phase such as, for example, cell division or elongation. Another application is the desirability of using tissue specific/preferred promoters and/or 3' UTRs/terminators to confine the expression of the transgenes encoding an agronomic trait in specific tissues types like developing parenchyma cells. As such, a particular problem in the identification of promoters and/or 3' UTRs/terminators is how to identify the promoters, and to relate the identified promoter to developmental properties of the cell for specific/preferred tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." *Genome research* 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." *Molecular biotechnology* 56.1 (2014): 38-49). Accordingly, the identification of promoter regulatory elements requires that an appropriate sequence of a specific size containing the necessary cis- and trans-regulatory elements is obtained that will result in driving expression of an operably linked transgene/heterologous coding sequence in a desirable manner.

Provided are methods and compositions for overcoming such problems through the use of GmCAB2 gene regulatory elements to express transgenes in planta.

II. Terms and Abbreviations

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence sequence has been introduced into a host cell by genetic engineering (or the progeny thereof) where the transgene/heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-GmCAB2 transgene" or "non-GmCAB2 gene" is any transgene/heterologous coding sequence that has less than 80% sequence identity with the GmCAB2 gene coding sequence of Glyma14g01130 as provided in UniProt Nucleotide Database as UniProtKB-C6TD73 SOYBN.

As used herein, "heterologous DNA coding sequence" means any coding sequence other than the one that naturally encodes the GmCAB2 gene, or any homolog of the expressed GmCAB2 protein. The term "heterologous" is used in the context of this invention for any combination of nucleic acid sequences that is not normally found intimately associated in nature.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007) Planta 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query) polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present invention is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the invention, function of a query polypeptide is inferred from function of a protein homolog where either (1) hit_p<1e-30 or % identity >35% AND query_coverage>50% AND hit coverage >50%, or (2) hit_p<1e-8 AND query_coverage>70% AND hit coverage >70%. The following abbreviations are produced during a BLAST analysis of a sequence.

| | |
|---|---|
| SEQ_NUM | provides the SEQ ID NO for the listed recombinant polynucleotide sequences. |
| CONTIG_ID | provides an arbitrary sequence name taken from the name of the clone from which the cDNA sequence was obtained. |
| PROTEIN_NUM | provides the SEQ ID NO for the recombinant polypeptide sequence |
| NCBI_GI | provides the GenBank ID number for the top BLAST hit for the sequence. The top BLAST hit is indicated by the National Center for Biotechnology Information GenBank Identifier number. |
| NCBI_GI_DESCRIPTION | refers to the description of the GenBank top BLAST hit for the sequence. |
| E_VALUE | provides the expectation value for the top BLAST match. |
| MATCH_LENGTH | provides the length of the sequence which is aligned in the top BLAST match |
| TOP_HIT_PCT_IDENT | refers to the percentage of identically matched nucleotides (or residues) that exist along the length of that portion of the sequences which is aligned in the top BLAST match. |
| CAT_TYPE | indicates the classification scheme used to classify the sequence. GO_BP = Gene Ontology Consortium-biological process; GO_CC = Gene Ontology Consortium-cellular component; GO_MF = Gene Ontology Consortium-molecular function; KEGG = KEGG functional hierarchy (KEGG = Kyoto Encyclopedia of Genes and Genomes); EC = Enzyme Classification from ENZYME data bank release 25.0; POI = Pathways of Interest. |
| CAT_DESC | provides the classification scheme subcategory to which the query sequence was assigned. |
| PRODUCT_CAT_DESC | provides the FunCAT annotation category to which the query sequence was assigned. |
| PRODUCT_HIT_DESC | provides the description of the BLAST hit which resulted in assignment of the sequence to the function category provided in the cat_desc column. |
| HIT_E | provides the E value for the BLAST hit in the hit_desc column. |
| PCT_IDENT | refers to the percentage of identically matched nucleotides (or residues) that exist along the length of that portion of the sequences which is aligned in the BLAST match provided in hit_desc. |
| QRY_RANGE | lists the range of the query sequence aligned with the hit. |
| HIT_RANGE | lists the range of the hit sequence aligned with the query. |
| QRY_CVRG | provides the percent of query sequence length that matches to the hit (NCBI) sequence in the BLAST match (% qry cvrg = (match length/query total length) × 100). |
| HIT_CVRG | provides the percent of hit sequence length that matches to the query sequence in the match generated using BLAST (% hit cvrg = (match length/hit total length) × 100). |

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, Calif.). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ (®1993-2016). DNASTAR. Madison, Wis.). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. Dec. 15; 73(1):237-44; Higgins and Sharp (1989) CABIOS 5:151-3; Higgins et al. (1992) Comput. Appl. Biosci. 8:189-91). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) J. Mol. Biol. 215:403-10). In an embodiment, the subject disclosure relates to calculating percent identity between two polynucleotides or amino acid sequences using the FASTA suite of alignment programs, including, but not limited to, FASTA, TFASTX, TFASTY, SSEARCH, LALIGN etc. (Pearson (1994) Comput. Methods Genome Res. [Proc. Int. Symp.], Meeting Date 1992 (Suhai and Sandor, Eds.), Plenum: New York, N.Y., pp. 111-20). In an embodiment, the subject disclosure relates to calculating percent identity between two polynucleotides or amino acid sequences using the EMBOSS suite of alignment programs, including, but not limited to: Matcher, Needle, Stretcher, Water, Wordmatch, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Geneious alignment program (Kearse, M., et. al. (2012). Geneious Basic: an integrated and extendable desktop software platform for the organization and analysis of sequence data. *Bioinformatics,* 28(12), 1647-49). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics,* 2:482-489, 1981, Smith et al., *Nucleic Acids Research* 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%>, 55%, 60%, 65%, 70%, 75%, 80%, 85%, 90%, 91%, 92%, 93%, 94%, 95%, 96%, 97%, 98% o, 99% or more sequence identity to that particular nucleotide sequence as determined by sequence alignment programs and parameters described elsewhere herein. A biologically active variant of a nucleotide sequence of the invention may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5' UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.,* 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "transcription terminator" or "terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALEN binding domains that can be "engineered" to bind to a predetermined nucleotide sequence. Typically, the engineered DNA binding proteins (e.g., zinc fingers, CRISPRs, or TALENs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALEN designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than different effector proteins into the plant cell. Among these injected proteins are transcription activator-like (TALEN) effectors which mimic plant transcriptional activators and manipulate the plant transcriptome (see Kay et al., (2007) Science 318:648-651). These proteins contain a DNA binding domain and a transcriptional activation domain. One of the most well characterized TAL-effectors is AvrBs3 from *Xanthomonas campestgris* pv. Vesicatoria (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). In other examples, the crRNA associates with the tracrRNA to guide the Cpf1 nuclease to a region homologous to the crRNA to cleave DNA with staggered ends (see Zetsche, Bernd, et al. *Cell* 163.3 (2015): 759-771.). Thus, the CRISPR/Cas system can be engineered to create a DSB at a desired target in a genome, and repair of the DSB can be influenced by the use of repair inhibitors to cause an increase in error prone repair.

In other examples, the DNA binding transgene/heterologous coding sequence is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441: 656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) *Cell* 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene/heterologous coding sequence is a gene sequence (e.g., an herbicide-resistance gene), a gene encoding an industrially or pharmaceutically useful compound, or a gene encoding a desirable agricultural trait. In yet another example, the transgene/heterologous coding sequence is an antisense nucleic acid sequence, wherein expression of the antisense nucleic acid sequence inhibits expression of a target nucleic acid sequence. A transgene/heterologous coding sequence may contain regulatory sequences operably linked to the transgene/heterologous coding sequence (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene/heterologous coding sequence of interest, regeneration of a population of plants resulting from the insertion of the transgene/heterologous coding sequence into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene/heterologous coding sequence DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene/heterologous coding sequence of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (TexasRed®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, Salt KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mot Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA),"

"diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

III. GmCAB2 Gene Regulatory Elements and Nucleic Acids Comprising the Same

Provided are methods and compositions for using a promoter from a *Glycine max* Glyma10g39460 (Photosystem I subunit PsaD) gene to express non-GmCAB2 transgenes in plant. In an embodiment, a promoter can be the GmCAB2 gene promoter of SEQ ID NO:2, SEQ ID NO:28, or SEQ ID NO:29.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:2, SEQ ID NO:28, or SEQ ID NO:29. In an embodiment, a promoter is a GmCAB2 gene promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:2, SEQ ID NO:28, or SEQ ID NO:29. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:2, SEQ ID NO:28, or SEQ ID NO:29. In an embodiment, a nucleic acid vector is provided comprising a GmCAB2 promoter of SEQ ID NO:2, SEQ ID NO:28, or SEQ ID NO:29. In an embodiment, a polynucleotide is provided comprising a GmCAB2 promoter that is operably linked to a polylinker. In an embodiment, a gene expression cassette is provided comprising a GmCAB2 promoter that is operably linked to a non-GmCAB2 transgene. In an embodiment, a nucleic acid vector is provided comprising a GmCAB2 promoter that is operably linked to a non-GmCAB2 transgene. In one embodiment, the promoter consists of SEQ ID NO:2, SEQ ID NO:28, or SEQ ID NO:29. In an illustrative embodiment, a nucleic acid vector comprises a GmCAB2 promoter that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Transgene expression may also be regulated by a 5' UTR region located downstream of the promoter sequence. Both a promoter and a 5' UTR can regulate transgene/heterologous coding sequence expression. While a promoter is necessary to drive transcription, the presence of a 5' UTR can increase expression levels resulting in mRNA transcript for translation and protein synthesis. A 5' UTR gene region aids stable expression of a transgene. In a further embodiment an 5' UTR is operably linked to a GmCAB2 promoter. In an embodiment, a 5' UTR can be the GmCAB2 5' UTR of SEQ ID NO:3.

In an embodiment, a polynucleotide is provided comprising a 5' UTR, wherein the 5' UTR is at least 80%, 85%, 90%, 91%, 92%, 93%, 94%, 95%, 96%, 97%, 98%, 99%, 99.5%, 99.8%, or 100% identical to SEQ ID NO:3. In an embodiment, a 5' UTR is a GmCAB2 5' UTR comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, a nucleic acid vector is provided comprising GmCAB2 5' UTR of SEQ ID NO:3. In an embodiment, a polynucleotide is provided comprising a GmCAB2 5' UTR that is operably linked to a polylinker. In an embodiment, a gene expression cassette is provided comprising a GmCAB2 5' UTR that is operably linked to a non-GmCAB2 transgene. In an embodiment, a nucleic acid vector is provided comprising a GmCAB2 5' UTR that is operably linked to a non-GmCAB2 transgene. In one embodiment, the 5' UTR consists of SEQ ID NO:3. In an illustrative embodiment, a nucleic acid vector comprises a GmCAB2 5' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

Transgene expression may also be regulated by an intron region located downstream of the promoter sequence. Both a promoter and an intron can regulate transgene/heterologous coding sequence expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a GmCAB2 promoter.

In accordance with one embodiment a nucleic acid vector is provided comprising a recombinant gene expression cassette wherein the recombinant gene expression cassette comprises a GmCAB2 promoter operably linked to a polylinker sequence, a non-GmCAB2 gene or non-GmCAB2 transgene or combination thereof. In one embodiment the recombinant gene cassette comprises a GmCAB2 promoter operably linked to a non-GmCAB2 gene or transgene. In one embodiment the recombinant gene cassette comprises a GmCAB2 promoter as disclosed herein is operably linked to a polylinker sequence. The polylinker is operably linked to the GmCAB2 promoter in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmCAB2 promoter and a non-GmCAB2 gene. In an embodiment, the GmCAB2 promoter of SEQ ID NO: 2, SEQ ID NO:28, or SEQ ID NO:29 is operably linked to the 5' end of the non-GmCAB2 gene or transgene. In a further embodiment the GmCAB2 promoter sequence comprises SEQ ID NO:2, SEQ ID NO:28, or SEQ ID NO:29 or a sequence that has 80, 85, 90, 95, 99 or 100% sequence identity with SEQ ID NO:2, SEQ ID NO:28, or SEQ ID NO:29. In accordance with one embodiment a nucleic acid vector is provided comprising a gene cassette that consists of a GmCAB2 promoter, a non-GmCAB2 gene, wherein the GmCAB2 promoter is operably linked to the 5' end of the non-GmCAB2 gene, and the GmCAB2 promoter sequence comprises SEQ ID NO:2, SEQ ID NO:28, or SEQ ID NO:29 or a sequence that has 80, 85, 90, 95, 99 or 100% sequence identity with SEQ ID NO: 2, SEQ ID NO:28, or SEQ ID NO:29. In a further embodiment the GmCAB2 promoter sequence consists of SEQ ID NO: 2, or a 1,299 bp sequence that has 80, 85, 90, 95, or 99% sequence identity with SEQ ID NO: 2. In a further embodiment the GmCAB2 promoter sequence consists of SEQ ID NO: 28, or a 1,453 bp sequence that has 80, 85, 90, 95, or 99% sequence identity with SEQ ID NO: 28. In a further embodiment the GmCAB2 promoter sequence consists of SEQ ID NO: 29, or a 1,454 bp sequence that has 80, 85, 90, 95, or 99% sequence identity with SEQ ID NO: 29.

In accordance with one embodiment a nucleic acid vector is provided comprising a recombinant gene expression cassette wherein the recombinant gene expression cassette comprises a GmCAB2 5' UTR operably linked to a polylinker sequence, a non-GmCAB2 gene or transgene or combination thereof. In one embodiment the recombinant gene cassette comprises a GmCAB2 5' UTR operably linked to a non-GmCAB2 gene or transgene. In one embodiment the recombinant gene cassette comprises a GmCAB2 5' UTR as disclosed herein is operably linked to a polylinker sequence. The polylinker is operably linked to the GmCAB2 5' UTR in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmCAB2 5' UTR and a non-GmCAB2 gene. In an embodiment, the GmCAB2 5' UTR of SEQ ID NO:3 is operably linked to the 5' end of the non-GmCAB2 gene or transgene. In a further embodiment the GmCAB2 5' UTR sequence comprises SEQ ID NO:3 or a sequence that has 80, 85, 90, 95, 99 or 100% sequence identity with SEQ ID NO:3. In accordance with one embodiment a nucleic acid vector is provided comprising a gene cassette that consists of a GmCAB2 5' UTR, a non-GmCAB2 gene, wherein the GmCAB2 5' UTR is operably linked to the 5' end of the non-GmCAB2 gene, and the GmCAB2 gene 5' UTR sequence comprises SEQ ID NO:3 or a sequence that has 80, 85, 90, 95, 99 or 100% sequence identity with SEQ ID NO:3. In a further embodiment the GmCAB2 gene 5' UTR sequence consists of SEQ ID NO:3, or a 124 bp sequence that has 80, 85, 90, 95, or 99% sequence identity with SEQ ID NO:3.

A GmCAB2 promoter may also comprise one or more additional sequence elements. In some embodiments, a GmCAB2 promoter may comprise an exon (e.g., a leader or signal peptide such as a chloroplast transit peptide or ER retention signal). For example and without limitation, a GmCAB2 promoter may encode an exon incorporated into the GmCAB2 promoter as a further embodiment.

Further provided are methods and compositions for using a 3' UTR from a *Glycine max* Glyma10g39460 (Photosystem I subunit PsaD) gene to terminate the expression of non-GmCAB2 transgenes in a plant. In an embodiment, a 3' UTR terminator can be the GmCAB2 3' UTR of SEQ ID NO:4.

In an embodiment, a polynucleotide is provided comprising a 3' UTR, wherein the 3' UTR is at least 80%, 85%, 90%, 91%, 92%, 93%, 94%, 95%, 96%, 97%, 98%, 99%, 99.5%, 99.8%, or 100% identical to SEQ ID NO:4. In an embodiment, a 3' UTR is a GmCAB2 3' UTR comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:4. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:4. In an embodiment, a nucleic acid vector is provided comprising a GmCAB2 3' UTR of SEQ ID NO:4. In an embodiment, a polynucleotide is provided comprising a GmCAB2 3' UTR that is operably linked to a polylinker. In an embodiment, a gene expression cassette is provided comprising a GmCAB2 3' UTR that is operably linked to a non-GmCAB2 transgene. In an embodiment, a nucleic acid vector is provided comprising a GmCAB2 3' UTR that is operably linked to a non-GmCAB2 transgene. In one embodiment, the 3' UTR consists of SEQ ID NO: 4. In an illustrative embodiment, a nucleic acid vector comprises a GmCAB2 gene 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a GmCAB2 3'UTR operably linked to a polylinker sequence, a non-GmCAB2 gene or transgene/heterologous coding sequence or combination thereof. In one embodiment the recombinant gene cassette comprises a GmCAB2 3'UTR operably linked to a non-GmCAB2 gene or transgene. In one embodiment the recombinant gene cassette comprises a GmCAB2 3'UTR as disclosed herein is operably linked to a polylinker sequence. The polylinker is operably linked to the GmCAB2 3'UTR in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmCAB2 3'UTR and a non-GmCAB2 gene. In an embodiment, the GmCAB2 3'UTR of SEQ ID NO:4 is operably linked to the 3' end of the non-GmCAB2 gene or transgene. In a further embodiment the GmCAB2 3'UTR sequence comprises SEQ ID NO:4 or a sequence that has 80, 85, 90, 95, 99 or 100% sequence identity with SEQ ID NO:4. In accordance with one embodiment a nucleic acid vector is provided comprising a gene cassette that consists of a GmCAB2 3'UTR, a non-GmCAB2 gene, wherein the GmCAB2 3'UTR is operably linked to the 3' end of the non-GmCAB2 gene, and the GmCAB2 3'UTR sequence comprises SEQ ID NO:4 or a sequence that has 80, 85, 90, 95, 99 or 100% sequence identity with SEQ ID NO:4. In a further embodiment the GmCAB2 3'UTR sequence consists of SEQ ID NO:4, or a 278 bp sequence that has 80, 85, 90, 95, or 99% sequence identity with SEQ ID NO:4.

Further provided are methods and compositions for using a terminator from a *Glycine max* Glyma10g39460 (Photosystem I subunit PsaD) gene to terminate the expression of non-GmCAB2 transgenes in a plant. In an embodiment, a terminator can be the GmCAB2 terminator of SEQ ID NO:5.

In an embodiment, a polynucleotide is provided comprising a terminator, wherein the terminator is at least 80%, 85%, 90%, 91%, 92%, 93%, 94%, 95%, 96%, 97%, 98%, 99%, 99.5%, 99.8%, or 100% identical to SEQ ID NO:5. In an embodiment, a terminator is a GmCAB2 terminator comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:5. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:5. In an embodiment, a nucleic acid vector is provided comprising a GmCAB2 terminator of SEQ ID NO:5. In an embodiment, a polynucleotide is provided comprising a GmCAB2 terminator that is operably linked to a polylinker. In an embodiment, a gene expression cassette is provided comprising a GmCAB2 terminator that is operably linked to a non-GmCAB2 transgene. In an embodiment, a nucleic acid vector is provided comprising a GmCAB2 terminator that is operably linked to a non-GmCAB2 transgene. In one embodiment, the terminator consists of SEQ ID NO: 5. In an illustrative embodiment, a nucleic acid vector comprises a GmCAB2 terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a GmCAB2 terminator operably linked to a polylinker sequence, a non-GmCAB2 gene or transgene or combination thereof. In one embodiment the recombinant gene cassette comprises a GmCAB2 terminator operably linked to a non-GmCAB2 gene or transgene. In one embodiment the recombinant gene cassette comprises a GmCAB2 terminator as disclosed herein is operably linked to a polylinker sequence. The polylinker is operably linked to the GmCAB2 terminator in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a GmCAB2 terminator and a non-GmCAB2 gene. In an embodiment, the GmCAB2 terminator of SEQ ID NO:5 is operably linked to the 3' end of the non-GmCAB2 gene or transgene. In a further embodiment the GmCAB2 terminator sequence comprises SEQ ID NO:5 or a sequence that has 80, 85, 90, 95, 99 or 100% sequence identity with SEQ ID NO:5. In accordance with one embodiment a nucleic acid vector is provided comprising a gene cassette that consists of a GmCAB2 terminator, a non-GmCAB2 gene, wherein the GmCAB2 terminator is operably linked to the 3' end of the non-GmCAB2 gene, and the GmCAB2 terminator sequence comprises SEQ ID NO:5 or a sequence that has 80, 85, 90, 95, 99 or 100% sequence identity with SEQ ID NO:5. In a further embodiment the GmCAB2 terminator sequence consists of SEQ ID NO:5, or a 425 bp sequence that has 80, 85, 90, 95, or 99% sequence identity with SEQ ID NO:5.

In one embodiment a nucleic acid construct is provided comprising a GmCAB2 promoter and a non-GmCAB2 gene and optionally one or more of the following elements:
a) a 5' untranslated region;
b) an intron; and
c) a 3' untranslated region,
wherein,
the GmCAB2 promoter consists of SEQ ID NO:2, SEQ ID NO:28, SEQ ID NO:29, or a sequence having 95% sequence identity with SEQ ID NO:2, SEQ ID NO:28, or SEQ ID NO:29;
the GmCAB2 5'UTR consists of a known 5'UTR, SEQ ID NO:3, or a sequence having 95% sequence identity with SEQ ID NO:3; and
the 3' UTR consists of a known 3' UTR, SEQ ID NO:4 or a sequence having 95% sequence identity with SEQ ID NO:4; further wherein said GmCAB2 promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a GmCAB2 promoter and a non-GmCAB2 gene and optionally one or more of the following elements:
a) a 5' untranslated region;
b) an intron; and
c) a 3' terminator region,
wherein,
the GmCAB2 promoter consists of SEQ ID NO:2, SEQ ID NO:28, SEQ ID NO:29, or a sequence having 95% sequence identity with SEQ ID NO:2, SEQ ID NO:28, or SEQ ID NO:29;
the GmCAB2 5'UTR consists of a known 5'UTR, SEQ ID NO:3, or a sequence having 95% sequence identity with SEQ ID NO:3; and
the 3' terminator consists of a known 3' terminator, SEQ ID NO:5 or a sequence having 95% sequence identity with SEQ ID NO:5; further wherein said GmCAB2 promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

Another aspect of the subject disclosure comprises a functional variant which differs in one or more nucleotides from those of the nucleotide sequences comprising the regulatory element, provided herein. Such a variant is produced as the result of one or more modifications (e.g., deletion, rearrangement, or insertion) of the nucleotide sequences comprising the sequence described herein. For example, fragments and variants of the GmCAB2 promoter sequence of SEQ ID NO:2, SEQ ID NO:28, or SEQ ID NO:29 may be used in a DNA construct or in a gene expression cassette to drive expression of a heterologous coding sequence. As used herein, the term "fragment" refers to a portion of the nucleic acid sequence. Fragments of GmCAB2 promoter sequence of SEQ ID NO:2, SEQ ID NO:28, or SEQ ID NO:29 may retain the biological activity of initiating transcription, more particularly driving transcription in a tissue-preferred manner. Alternatively, fragments of a nucleotide sequence which are useful as hybridization probes may not necessarily retain biological activity. Fragments of a nucleotide sequence for the promoter region of the GmCAB2 promoter sequence of SEQ ID NO:2, SEQ ID NO:28, or SEQ ID NO:29 may range from at least about 20 nucleotides, about 50 nucleotides, about 100 nucleotides, up to the full-length nucleotide sequence of the invention for the promoter region of the gene.

A biologically active portion of a GmCAB2 promoter sequence of SEQ ID NO:2, SEQ ID NO:28, or SEQ ID NO:29 can be prepared by isolating a portion of the GmCAB2 promoter sequence of SEQ ID NO:2, SEQ ID NO:28, or SEQ ID NO:29, and assessing the promoter activity of the portion. Nucleic acid molecules that are fragments of an GmCAB2 promoter nucleotide sequence comprise at least about 16, 50, 75, 100, 150, 200, 250, 300, 350, 400, 450, 500, 550, 600, 650, 700, 800, 900, 1000, 1100, 1200, 1300, 1400, 1500, 1550, 1600, 1650, or 1700 nucleotides, or up to the number of nucleotides present in a full-length GmCAB2 promoter sequence disclosed herein.

Variant nucleotide sequences also encompass sequences derived from a mutagenic and recombinogenic procedure such as DNA shuffling. With such a procedure, GmCAB2 promoter nucleotide sequences of SEQ ID NO:2, SEQ ID NO:28, or SEQ ID NO:29 can be manipulated to create a new GmCAB2 promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA i: 10747-10751; Stemmer (1994) Nature 570:389-391; Crameri et al. (1997) Nature Biotech. 75:436-438; Moore et al. (1997) J. Mol. Biol. 272:336-347; Zhang et al. (1997) Proc. Natl. Acad. Sci. USA £4:4504-4509; Crameri et al. (1998) Nature 527:288-291; and U.S. Pat. Nos. 5,605,793 and 5,837,458.

The nucleotide sequences of the subject disclosure can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire GmCAB2 promoter sequence set forth herein or to fragments thereof are encompassed by the present invention.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.), hereinafter Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $P^{32}$ or any other detectable marker. Thus, for example, probes for hybridization can be made by labeling synthetic oligonucleotides based on the GmCAB2 promoter sequence of the invention. Methods for preparation of probes for hybridization and for construction of genomic libraries are generally known in the art and are disclosed in Sambrook. For example, the entire GmCAB2 promoter sequence disclosed herein, or one or more portions thereof, may be used as a probe capable of specifically hybridizing to corresponding GmCAB2 promote sequences and messenger RNAs. To achieve specific hybridization under a variety of conditions, such probes include sequences that are unique among GmCAB2 promoter sequence and are at least about 10 nucleotides in length or at least about 20 nucleotides in length. Such probes may be used to amplify corresponding GmCAB2 promoter sequence from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook).

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein the first T-DNA border is operably linked to one end of a gene construct, and the second T-DNA border is operably linked to the other end of a gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:2, SEQ ID NO:28, or SEQ ID NO:29 or a sequence having 80, 85, 90, 95, or 99% sequence identity with SEQ ID NO:2, SEQ ID NO:28, or SEQ ID NO:29. In another embodiment, the first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In an embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:3, or a sequence having 80, 85, 90, 95, or 99% sequence identity with SEQ ID NO:3. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:4 or a sequence having 80, 85, 90, 95, or 99% sequence identity with SEQ ID NO:4. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:5 or a sequence having 80, 85, 90, 95, or 99% sequence identity with SEQ ID NO:5.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene/heterologous coding sequence encodes a selectable marker or a gene product conferring insecticidal resistance, herbicide tolerance, small RNA expression, nitrogen use efficiency, water use efficiency, or nutritional quality.

1. Insect Resistance

Various insect resistance genes can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab(truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A (a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol', Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), ls+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the GmCAB2 promoter comprising SEQ ID NO: 2, SEQ ID NO:28, or SEQ ID NO:29, or a sequence that has 80, 85, 90, 95 or 99% sequence identity with SEQ ID NO: 2, SEQ ID NO:28, or SEQ ID NO:29. In addition, the insect resistance genes can be operably linked to the GmCAB2 5' UTR comprising SEQ ID NO:3, or a sequence that has 80, 85, 90, 95 or 99% sequence identity with SEQ ID NO:3. Likewise, the insect resistance genes can be operably linked to the GmCAB2 3' UTR comprising SEQ ID NO:4, or a sequence that has 80, 85, 90, 95 or 99% sequence identity with SEQ ID NO: 4. Furthermore, the insect resistance genes can be operably linked to the GmCAB2 terminator comprising SEQ ID NO:5, or a sequence that has 80, 85, 90, 95 or 99% sequence identity with SEQ ID NO: 5. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces* viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and ls+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvylshikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non *Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Transgenic Plants

In an embodiment, a plant, plant tissue, or plant cell comprises a GmCAB2 promoter. In one embodiment a plant, plant tissue, or plant cell comprises the GmCAB2 promoter of a sequence selected from SEQ ID NO:2, SEQ ID NO:28, or SEQ ID NO:29 or a sequence that has 80%, 85%, 90%, 95% or 99.5% sequence identity with a sequence selected from SEQ ID NO:2, SEQ ID NO:28, or SEQ ID NO:29. In an embodiment, a plant, plant tissue, or plant cell comprises a gene expression cassette comprising a sequence selected from SEQ ID NO:2, SEQ ID NO:28, or SEQ ID NO:29, or a sequence that has 80%, 85%, 90%, 95% or 99.5% sequence identity with a sequence selected from SEQ ID NO:2, SEQ ID NO:28, or SEQ ID NO:29 that is operably linked to a non-GmCAB2 gene. In an illustrative embodiment, a plant, plant tissue, or plant cell comprises a gene expression cassette comprising a GmCAB2 promoter that is operably linked to a transgene or heterologous coding sequence, wherein the transgene or heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmCAB2 promoter derived sequence operably linked to a transgene, wherein the GmCAB2 promoter derived sequence comprises a sequence SEQ ID NO:2, SEQ ID NO:28, or SEQ ID NO:29 or a sequence having 80%, 85%, 90%, 95% or 99.5% sequence identity with SEQ ID NO:2. In one embodiment a plant, plant tissue, or plant cell is provided wherein the plant, plant tissue, or plant cell comprises SEQ ID NO:2, SEQ ID NO:28, or SEQ ID NO:29, or a sequence that has 80%, 85%, 90%, 95% or 99.5% sequence identity with SEQ ID NO:2, SEQ ID NO:28, or SEQ ID NO:29 operably linked to a non-GmCAB2 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine*

*max*). In accordance with one embodiment the plant, plant tissue, or plant cell comprises SEQ ID NO:2, SEQ ID NO:28, or SEQ ID NO:29 or a sequence having 80%, 85%, 90%, 95% or 99.5% sequence identity with SEQ ID NO:2, SEQ ID NO:28, or SEQ ID NO:29 operably linked to a non-GmCAB2 gene. In one embodiment the plant, plant tissue, or plant cell comprises a promoter operably linked to a transgene/heterologous coding sequence wherein the promoter consists of SEQ ID NO:2, SEQ ID NO:28, or SEQ ID NO:29 or a sequence having 80%, 85%, 90%, 95% or 99.5% sequence identity with SEQ ID NO:2, SEQ ID NO:28, or SEQ ID NO:29. In accordance with one embodiment the gene construct comprising GmCAB2 promoter sequence operably linked to a transgene/heterologous coding sequence is incorporated into the genome of the plant, plant tissue, or plant cell.

In an embodiment, a plant, plant tissue, or plant cell comprises a GmCAB2 5' UTR. In one embodiment a plant, plant tissue, or plant cell comprises the GmCAB2 5' UTR of a sequence selected from SEQ ID NO:3 or a sequence that has 80%, 85%, 90%, 95% or 99.5% sequence identity with a sequence selected from SEQ ID NO:3. In an embodiment, a plant, plant tissue, or plant cell comprises a gene expression cassette comprising a sequence selected from SEQ ID NO:3, or a sequence that has 80%, 85%, 90%, 95% or 99.5% sequence identity with a sequence selected from SEQ ID NO:3 that is operably linked to a non-GmCAB2 gene. In an illustrative embodiment, a plant, plant tissue, or plant cell comprises a gene expression cassette comprising a GmCAB2 5' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmCAB2 5' UTR derived sequence operably linked to a transgene, wherein the GmCAB2 5' UTR derived sequence comprises a sequence SEQ ID NO:3 or a sequence having 80%, 85%, 90%, 95% or 99.5% sequence identity with SEQ ID NO:3. In one embodiment a plant, plant tissue, or plant cell is provided wherein the plant, plant tissue, or plant cell comprises SEQ ID NO:3, or a sequence that has 80%, 85%, 90%, 95% or 99.5% sequence identity with SEQ ID NO:3 operably linked to a non-GmCAB2 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO:3 or a sequence having 80%, 85%, 90%, 95% or 99.5% sequence identity with SEQ ID NO:3 operably linked to a non-GmCAB2 gene. In one embodiment the plant, plant tissue, or plant cell comprises a 5' UTR operably linked to a transgene/heterologous coding sequence wherein the 5' UTR consists of SEQ ID NO:3 or a sequence having 80%, 85%, 90%, 95% or 99.5% sequence identity with SEQ ID NO:3. In accordance with one embodiment the gene construct comprising GmCAB2 5' UTR sequence operably linked to a transgene/heterologous coding sequence is incorporated into the genome of the plant, plant tissue, or plant cell.

In an embodiment, a plant, plant tissue, or plant cell comprises a GmCAB2 3' UTR. In one embodiment a plant, plant tissue, or plant cell comprises the GmCAB2 3' UTR of a sequence selected from SEQ ID NO:4 or a sequence that has 80%, 85%, 90%, 95% or 99.5% sequence identity with a sequence selected from SEQ ID NO:4. In an embodiment, a plant, plant tissue, or plant cell comprises a gene expression cassette comprising a sequence selected from SEQ ID NO:4, or a sequence that has 80%, 85%, 90%, 95% or 99.5% sequence identity with a sequence selected from SEQ ID NO:4 that is operably linked to a non-GmCAB2 gene. In an illustrative embodiment, a plant, plant tissue, or plant cell comprises a gene expression cassette comprising a GmCAB2 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmCAB2 3' UTR derived sequence operably linked to a transgene, wherein the GmCAB2 3' UTR derived sequence comprises a sequence SEQ ID NO:4 or a sequence having 80%, 85%, 90%, 95% or 99.5% sequence identity with SEQ ID NO:4. In one embodiment a plant, plant tissue, or plant cell is provided wherein the plant, plant tissue, or plant cell comprises SEQ ID NO:4, or a sequence that has 80%, 85%, 90%, 95% or 99.5% sequence identity with SEQ ID NO:4 operably linked to a non-GmCAB2 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO:4 or a sequence having 80%, 85%, 90%, 95% or 99.5% sequence identity with SEQ ID NO:4 operably linked to a non-GmCAB2 gene. In one embodiment the plant, plant tissue, or plant cell comprises a 3' UTR operably linked to a transgene/heterologous coding sequence wherein the 3' UTR consists of SEQ ID NO:4 or a sequence having 80%, 85%, 90%, 95% or 99.5% sequence identity with SEQ ID NO:4. In accordance with one embodiment the gene construct comprising GmCAB2 gene 3' UTR sequence operably linked to a transgene/heterologous coding sequence is incorporated into the genome of the plant, plant tissue, or plant cell.

In an embodiment, a plant, plant tissue, or plant cell comprises a GmCAB2 terminator. In one embodiment a plant, plant tissue, or plant cell comprises the GmCAB2 terminator of a sequence selected from SEQ ID NO:5 or a sequence that has 80%, 85%, 90%, 95% or 99.5% sequence identity with a sequence selected from SEQ ID NO:5. In an embodiment, a plant, plant tissue, or plant cell comprises a gene expression cassette comprising a sequence selected from SEQ ID NO:5, or a sequence that has 80%, 85%, 90%, 95% or 99.5% sequence identity with a sequence selected from SEQ ID NO:5 that is operably linked to a non-GmCAB2 gene. In an illustrative embodiment, a plant, plant tissue, or plant cell comprises a gene expression cassette comprising a GmCAB2 terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a GmCAB2 terminator derived sequence operably linked to a transgene, wherein the GmCAB2 terminator derived sequence comprises a sequence SEQ ID NO:5 or a sequence having 80%, 85%, 90%, 95% or 99.5% sequence identity with SEQ ID NO:5. In one embodiment a plant, plant tissue, or plant cell is provided wherein the plant, plant tissue, or plant cell comprises SEQ ID NO:5, or a sequence that has 80%, 85%, 90%, 95% or 99.5% sequence identity with SEQ ID NO:5 operably linked to a non-GmCAB2 gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO:5 or a sequence having 80%, 85%, 90%, 95% or 99.5% sequence identity with SEQ ID NO:5 operably linked to a non-GmCAB2 gene. In one embodiment the plant, plant tissue, or plant cell comprises a terminator operably linked to a transgene/heterologous coding sequence wherein the terminator consists of SEQ ID NO:5 or a sequence having 80%, 85%, 90%, 95% or 99.5% sequence identity with SEQ ID NO:5. In accordance with one embodiment the gene construct comprising GmCAB2 gene terminator sequence operably linked to a transgene/ heterologous coding sequence is incorporated into the genome of the plant, plant tissue, or plant cell.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene/heterologous coding sequence or gene construct containing the gene regulatory elements of the subject disclosure. The present disclosure further encompasses the progeny, clones, cell lines or cells of the transgenic plants described above wherein said progeny, clone, cell line or cell has the transgene/heterologous coding sequence or gene construct containing the gene regulatory elements of the subject disclosure.

The present disclosure also encompasses the cultivation of transgenic plants described above, wherein the transgenic plant has the transgene/heterologous coding sequence or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene/heterologous coding sequence in a plant comprises growing a plant comprising a GmCAB2 promoter operably linked to at least one transgene/heterologous coding sequence or a polylinker sequence. In an embodiment the GmCAB2 promoter consists of a sequence selected from SEQ ID NO:2, SEQ ID NO:28, or SEQ ID NO:29 or a sequence that has 80%, 85%, 90%, 95% or 99.5% sequence identity with a sequence selected from SEQ ID NO:2, SEQ ID NO:28, or SEQ ID NO:29. In an embodiment, a method of expressing at least one transgene/heterologous coding sequence in a plant comprising growing a plant comprising a GmCAB2 promoter operably linked to at least one transgene. In an embodiment, a method of expressing at least one transgene/heterologous coding sequence in a plant tissue or plant cell comprising culturing a plant tissue or plant cell comprising a GmCAB2 promoter operably linked to at least one transgene.

In an embodiment, a method of expressing at least one transgene/heterologous coding sequence in a plant comprises growing a plant comprising a gene expression cassette comprising a GmCAB2 promoter operably linked to at least one transgene. In one embodiment the GmCAB2 promoter consists of a sequence selected from SEQ ID NO:2, SEQ ID NO:28, or SEQ ID NO:29 or a sequence that has 80%, 85%, 90%, 95% or 99.5% sequence identity with a sequence selected from SEQ ID NO:2, SEQ ID NO:28, or SEQ ID NO:29. In an embodiment, a method of expressing at least one transgene/heterologous coding sequence in a plant comprises growing a plant comprising a gene expression cassette comprising a GmCAB2 promoter operably linked to at least one transgene. In an embodiment, a method of expressing at least one transgene/heterologous coding sequence in a plant comprises growing a plant comprising a gene expression cassette comprising a GmCAB2 promoter operably linked to at least one transgene. In an embodiment, a method of expressing at least one transgene/heterologous coding sequence in a plant tissue or plant cell comprises culturing a plant tissue or plant cell comprising a gene expression cassette containing a GmCAB2 promoter operably linked to at least one transgene. In an embodiment, a method of expressing at least one transgene/heterologous coding sequence in a plant tissue or plant cell comprises culturing a plant tissue or plant cell comprising a gene expression cassette, a GmCAB2 promoter operably linked to at least one transgene.

In an embodiment, a method of expressing at least one transgene/heterologous coding sequence in a plant comprises growing a plant comprising a GmCAB2 5' UTR operably linked to at least one transgene/heterologous coding sequence or a polylinker sequence. In an embodiment the GmCAB2 5' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprising growing a plant comprising a GmCAB2 5' UTR operably linked to at least one transgene. In an embodiment, a method of expressing at least one transgene/heterologous coding sequence in a plant tissue or plant cell comprising culturing a plant tissue or plant cell comprising a GmCAB2 5' UTR operably linked to at least one transgene.

In an embodiment, a method of expressing at least one transgene/heterologous coding sequence in a plant comprises growing a plant comprising a gene expression cassette comprising a GmCAB2 5' UTR operably linked to at least one transgene. In one embodiment the GmCAB2 5' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/ heterologous coding sequence in a plant comprises growing a plant comprising a gene expression cassette comprising a GmCAB2 5' UTR operably linked to at least one transgene. In an embodiment, a method of expressing at least one transgene/heterologous coding sequence in a plant comprises growing a plant comprising a gene expression cassette comprising a GmCAB2 5' UTR operably linked to at least one transgene. In an embodiment, a method of expressing at least one transgene/heterologous coding sequence in a plant tissue or plant cell comprises culturing a plant tissue or plant cell comprising a gene expression cassette containing a GmCAB2 5' UTR operably linked to at least one transgene. In an embodiment, a method of expressing at least one transgene/heterologous coding sequence in a plant tissue or plant cell comprises culturing a plant tissue or plant cell comprising a gene expression cassette, a GmCAB2 5' UTR operably linked to at least one transgene.

In an embodiment, a method of expressing at least one transgene/heterologous coding sequence in a plant comprises growing a plant comprising a GmCAB2 3' UTR operably linked to at least one transgene/heterologous coding sequence or a polylinker sequence. In an embodiment the GmCAB2 3' UTR consists of a sequence selected from SEQ ID NO:4 or a sequence that has 80%, 85%, 90%, 95% or 99.5% sequence identity with a sequence selected from SEQ ID NO:4. In an embodiment, a method of expressing at least one transgene/heterologous coding sequence in a plant comprising growing a plant comprising a GmCAB2 3' UTR operably linked to at least one transgene. In an embodiment, a method of expressing at least one transgene/heterologous coding sequence in a plant tissue or plant cell comprising culturing a plant tissue or plant cell comprising a GmCAB2 3' UTR operably linked to at least one transgene.

In an embodiment, a method of expressing at least one transgene/heterologous coding sequence in a plant comprises growing a plant comprising a gene expression cassette comprising a GmCAB2 3' UTR operably linked to at least one transgene. In one embodiment the GmCAB2 3' UTR consists of a sequence selected from SEQ ID NO:4 or a sequence that has 80%, 85%, 90%, 95% or 99.5% sequence identity with a sequence selected from SEQ ID NO:4. In an embodiment, a method of expressing at least one transgene/ heterologous coding sequence in a plant comprises growing a plant comprising a gene expression cassette comprising a GmCAB2 3' UTR operably linked to at least one transgene. In an embodiment, a method of expressing at least one transgene/heterologous coding sequence in a plant comprises growing a plant comprising a gene expression cassette comprising a GmCAB2 3' UTR operably linked to at least one transgene. In an embodiment, a method of expressing at least one transgene/heterologous coding sequence in a plant tissue or plant cell comprises culturing a plant tissue or plant cell comprising a gene expression cassette containing a GmCAB2 3' UTR operably linked to at least one transgene. In an embodiment, a method of expressing at least one transgene/heterologous coding sequence in a plant tissue or plant cell comprises culturing a plant tissue or plant cell comprising a gene expression cassette, a GmCAB2 3' UTR operably linked to at least one transgene.

In an embodiment, a method of expressing at least one transgene/heterologous coding sequence in a plant comprises growing a plant comprising a GmCAB2 terminator operably linked to at least one transgene/heterologous coding sequence or a polylinker sequence. In an embodiment the GmCAB2 terminator consists of a sequence selected from SEQ ID NO:5 or a sequence that has 80%, 85%, 90%, 95% or 99.5% sequence identity with a sequence selected from SEQ ID NO:5. In an embodiment, a method of expressing at least one transgene/heterologous coding sequence in a plant comprising growing a plant comprising a GmCAB2 terminator operably linked to at least one transgene. In an embodiment, a method of expressing at least one transgene/heterologous coding sequence in a plant tissue or plant cell comprising culturing a plant tissue or plant cell comprising a GmCAB2 terminator operably linked to at least one transgene.

In an embodiment, a method of expressing at least one transgene/heterologous coding sequence in a plant comprises growing a plant comprising a gene expression cassette comprising a GmCAB2 terminator operably linked to at least one transgene. In one embodiment the GmCAB2 terminator consists of a sequence selected from SEQ ID NO:5 or a sequence that has 80%, 85%, 90%, 95% or 99.5% sequence identity with a sequence selected from SEQ ID NO:5. In an embodiment, a method of expressing at least one transgene/heterologous coding sequence in a plant comprises growing a plant comprising a gene expression cassette comprising a GmCAB2 terminator operably linked to at least one transgene. In an embodiment, a method of expressing at least one transgene/heterologous coding sequence in a plant comprises growing a plant comprising a gene expression cassette comprising a GmCAB2 terminator operably linked to at least one transgene. In an embodiment, a method of expressing at least one transgene/heterologous coding sequence in a plant tissue or plant cell comprises culturing a plant tissue or plant cell comprising a gene expression cassette containing a GmCAB2 terminator operably linked to at least one transgene. In an embodiment, a method of expressing at least one transgene/heterologous coding sequence in a plant tissue or plant cell comprises culturing a plant tissue or plant cell comprising a gene expression cassette, a GmCAB2 terminator operably linked to at least one transgene.

The following examples are provided to illustrate certain particular features and/or embodiments. The examples should not be construed to limit the disclosure to the particular features or embodiments exemplified.

EXAMPLES

Example 1: Identification of Regulatory Elements from Soybean Genomic Sequences

The expression profiles of total mRNA expression for 25 soybean tissues (var. Williams 82) were obtained via Next Generation Sequencing (NGS) and were used to identify candidate soybean genes for sourcing regulatory elements. The tissues included were collected from young seedlings (expanded cotyledons, roots, and hypocotyls), V5 (leaves and stems), and R5 (leaves, flowers, different stages of seed and pod development) soybean plants. Soybean endogenous genes that exhibited the desired expression profile were identified as potential candidates for sourcing regulatory sequences.

One of the genes with the desired expression pattern was Glyma14g01130 that was expressed in green tissues. This gene was identified as the GmCAB2 gene encoding Chlorophyll a/b binding protein type II (UniProtKB-C6TD73 SOYBN) (Apweiler, Rolf, et al. "UniProt: the universal protein knowledgebase." *Nucleic acids research* 32.suppl_1 (2004): D115-D119; available at the uniport.org website), thus this gene was described here as "GmCAB2". Regulatory sequences from the GmCAB2 gene were isolated and characterized for the ability to drive transgene expression. The promoter of the GmCAB2 is provided herein as SEQ ID NO:2.

The regulatory sequences of the Glyma14g01130 gene (GmCAB2) were defined as ~1.5 kb sequence upstream of ATG of the Glyma14g01130 gene for the promoter and 5' untranslated leader (UTR), and ~0.4 kb downstream of the Glyma14g01130 gene stop codon for the 3' UTR and terminator. To further refine the regulatory sequences additional analyses of the regulatory elements were completed. Putative upstream and downstream regulatory sequences were assessed for the presence of transposable sequences, repressive DNA (methylation) and chromatin (histone-H3-lysine-4-dimethylation, commonly abbreviated as H3K4me2) marks using methods as previously disclosed in U.S. Patent Publication No. 20150128309A1, herein incorporated by reference in its entirety. The Glyma14g01130 gene DNA sequences containing the repressive DNA and chromatin marks were excluded from the sourced upstream and downstream regulatory sequence. Long stretches (100 bp or more) of AT-rich sequences (>75% AT rich) within the 5' and 3' sequences were also avoided as means to reduce difficulties with de novo synthesis of the DNA fragments.

The resulting GmCAB2 upstream regulatory sequence contained both a promoter (SEQ ID NO:2) and 5' UTR (SEQ ID NO:3). The downstream sequences encompassed a 3' UTR (SEQ ID NO:4) and a terminator (SEQ ID NO:5) of the GmCAB2 gene. The terminator sequences extended for ~100-200 bp beyond the last known poly-adenylation site.

Sequences of the sourced from soybean genome the GmCAB2 (Glyma14g01130) gene promoter/5'UTR and terminator are provided in the sequence listing:

Additional candidate regulatory sequences that were sourced from soybean were: Glyma06g15520 annotated as encoding actin-like protein (Dai, Xinbin, Ji He, and Xuechun Zhao. "A new systematic computational approach to predicting target genes of transcription factors." *Nucleic acids research* 35.13 (2007): 4433-4440) which we named as GmAct7-2 (SEQ ID NO:6) and Glyma06g18110 annotated as encoding Glyceraldehyde-3-phosphate dehydrogenase C1 (Dai, Xinbin, Ji He, and Xuechun Zhao. "A new systematic computational approach to predicting target genes of transcription factors." *Nucleic acids research* 35.13 (2007): 4433-4440) and we named this gene as GmGAPC1 (SEQ ID NO:7). The additional regulatory sequences from the Glyma06g15520 and Glyma06g18110 were sourced using the same approach as that described for GmCAB2. In addition minor modifications were made by removing a couple of base pairs from the regulatory sequences of the Glyma06g15520 and Glyma06g18110 promoters to facilitate cloning of the promoters into gene expression cassettes.

Example 2: Cloning of the Regulatory Sequences from Soybean

The promoter, 5' UTR and 3' UTR/terminator sequences of the GmCAB2 gene were synthesized by DNA2.0. A diagram of the synthetic fragment is shown in FIG. 1. A linker containing multiple cloning site was included between the promoter/5' UTR and the 3' UTR/terminator sequence.

Figure 2:
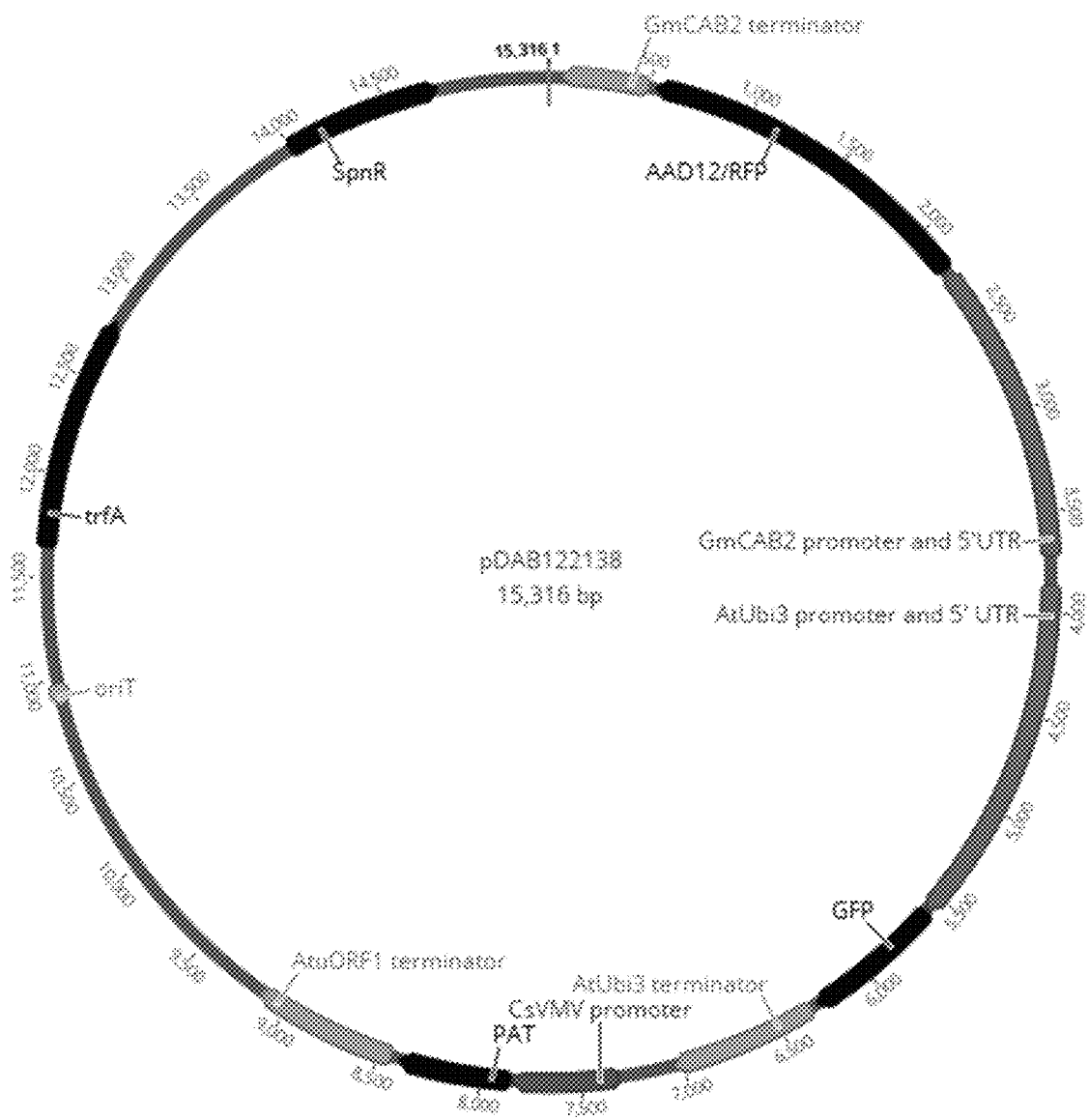
FIG. 2. Provides a figure of a plasmid map of pDAB122135.

The synthetic GmCAB2 fragment (promoter/5'UTR and terminator) was cloned in a Gateway entry vector, and the RFP/AAD12 reporter gene (SEQ ID NO:10) was inserted between the 5'UTR and the terminator. The reporter gene was the dual reporter encoding a translational fusion protein containing the RFP and AAD12 polypeptides joined with the rigid helical peptide linker, LAE(EAAAK)$_5$AAA described by Arai et al, (2001), Protein Eng, 14, 529-532 and Marqusee et al, (1987), Proc Natl Acad Sci USA, 84, 8898-8902. The resulting expression cassette (SEQ ID NO:11) was moved to a binary vector and labeled as pDAB122138 (FIG. 2). This binary vector also contained the Green Fluorescent Protein (GFP) gene driven by the *Arabidopsis* Ubiquitin3 promoter and 5' UTR (AtUbi3) and terminated by the *Arabidopsis* Ubiquitin 3 terminator (AtUbi3). Likewise, the binary vector contained the synthetic phosphinothricin N-acetyltransferase gene from *Streptomyces viridochromogenes* (PAT) was driven by the Cassava vein mosaic virus promoter (CsVMV) and terminated by the *Agrobacterium tumefaciens* Orf1 terminator (AtuOrf1). The GFP and PAT gene expression cassettes are provided as SEQ ID NO:12.

Cloning steps for the GmAct7-2 and GmGAPC1 regulatory sequences were similar to those described above for GmCAB2. The GmAct7-2 was tested in the pDAB122133 construct and GmGAPC1 was tested in the pDAB122134 construct.

Example 3: *N. benthamiana* Leaf Infiltrations and Transient Assays of GmCAB2, GmAct7-2 and GmGAPC1 Driven Expression of the RFP/AAD12 Reporter Next, *N. benthamiana* plants were grown in the greenhouse under a 16 hour photoperiod, 27° C./24° C. The 20-24 day old plants were used for transient expression assays. For this, the top 3-4 leaves were infiltrated using a mix of two modified *Agrobacterium tumefaciens* strains. The first strain was used in all infiltrations and carried the pDAB112236 construct containing transgene that expressed the P19 silencing suppressor (Voinnet et al, (1999), Proc Natl Acad Sci U.S.A., 96, 14147-14152). The second *Agrobacterium* strain was either the experimental strain carrying a test construct (with the GmCAB2, GmAct7-2, or GmGAPC1 regulatory elements), or a benchmark control construct (Table 1). Two benchmark constructs that were used contained the RFP/AAD12 reporter gene under the control of *Arabidopsis thaliana* Ubiquitin 14 promoter::*Arabidopsis thaliana* Ubiquitin 14 terminator (AtUbi14/AtUbi14) and the *Arabidopsis thaliana* Ubiquitin 10 promoter::*Agrobacterium tumefaciens* Orf23 (AtUbi10/AtuOrf23). The mixing ratios were based on Optical Density (OD) readings. The density of all *Agrobacterium* cultures was adjusted to OD 2.0. After infiltration, plants were grown in a Conviron™ until the infiltrated leaves were collected on the fifth day after infiltration.

Fluorescence data for the reporter genes was collected using a Typhoon™ scanner from multiple individual 1.5 cm leaf disks for each construct.

All samples from *N. benthamiana* were scanned on three channels; chlorophyll (488 nm blue laser, 670 nm BP30, 580 nm split), GFP (488 nm blue laser, 520 nm BP40, 580 nm split), and RFP (532 nm green laser, 580 nm BP30). The photomultiplier voltage (PMT) setting used for *N. benthamiana* was 340 for chlorophyll, 340 for GFP and 360 for RFP.

tory sequences from Glyma06g15520 and Glyma06g18110 were not capable of driving heterologous reporter transgene expression.

Based on these results, constructs pDAB122333 and pDAB122134 carrying GmAct7-2 and GmGAPC1, respectively, were not pursued further. In contrast, the pDAB122138 construct containing the GmCAB2 regulatory sequences and exhibiting high levels of RFP/AAD12 fluorescence, as compared to background fluorescence of the *N. benthamiana* leaves, was advanced for further testing in stably transformed *Arabidopsis* transgenic plants.

TABLE 1

Results of assaying RFP/AAD12 fluorescence in transiently transformed *N. benthamiana* leaves.

| Construct | Regulatory Element name | No. of samples | RFP fluorescence (pixels/area) | | | | GFP fluorescence (pixels/area) | | | |
|---|---|---|---|---|---|---|---|---|---|---|
| | | | Mean | Median | Std Dev | Std Err | Mean | Median | Std Dev | Std Err |
| P19 only | None (Background) | 216 | 26.1 | 24.0 | 14.4 | 1.0 | 34.6 | 33.5 | 14.0 | 1.0 |
| pDAB 117559 | AtUbi14/ AtUbi14 | 261 | 7567.4*** | 6698.4 | 5191.7 | 321.4 | 9770.9*** | 9230.0 | 4609.7 | 285.3 |
| pDAB 117560 | AtUbi10/ AtuOrf23 | 260 | 3084.5*** | 2760.0 | 1984.2 | 123.1 | 8915.9*** | 8737.2 | 5404.7 | 335.2 |
| pDAB 122133 | GmAct7-2/ GmAct7-2 | 60 | 25.3 | 26.4 | 7.0 | 0.9 | 14206.1*** | 12874.3 | 6178.5 | 797.6 |
| pDAB 122134 | GmGAPC1/ GmGAPC1 | 30 | 25.3 | 24.6 | 5.1 | 0.9 | 5295.7*** | 5184.5 | 2085.8 | 380.8 |
| pDAB 122138 | GmCAB2/ GmCAB2 | 90 | 473.2*** | 386.7 | 313.0 | 33.0 | 5904.0*** | 5262.2 | 3414.9 | 360.0 |

Note:
***indicates RFP or GFP means that are significantly higher (p < 0.0001) than the mean background fluorescence. Due to presence of unequal variances, Welch t-test was used to compare mean RFP or GFP fluorescence of each construct to the corresponding fluorescence means of "P19 only" background control. Statistical analyses were conducted using JMP ® statistical package.

Results of testing in *N. benthamiana* transient assay are shown in Table 1. Analysis of fluorescence produced by RFP/AAD12 reporter transgene revealed that the GmCAB2 regulatory sequences resulted in mean RFP fluorescence (473.2 pixels/area) that was significantly higher (p<0.0001) than mean background fluorescence (26.1 pixels/area). It was observed that the RFP/AAD12 fluorescence from the GmCAB2 regulatory sequences was lower (p<0.0001) than the mean RFP/AAD12 fluorescence from the constructs driven by the benchmark regulatory elements of the AtUbi14/AtUbi14 and the AtUbi10/AtuOrf23; 7567.4 and 3084.5 pixels/area, respectively. The significantly higher than background RFP/AAD12 fluorescence supported by the GmCAB2 regulatory elements indicated that the GmCAB2 regulatory sequences from Glyma14g01130 were functional and can be used to drive expression of a heterologous transgene in *N. benthamiana* leaf transient assays.

In contrast, to the GmCAB2 regulatory sequences which drove significantly higher than background mean RFP/AAD12 fluorescence expression, the GmAct2-2 and GmGAPC1 regulatory sequences contained within the pDAB122333 and pDAB122134 constructs, respectively, produced only low levels of expression that was similar to the background (Table 1). These results demonstrate that the de novo isolated GmAct2-2 and GmGAPC1 candidate soybean regulatory sequences were not able to drive RFP/AAD12 transgene expression. Lack of RFP/AAD12 expression in the pDAB122333 and pDAB122134 constructs was not due to poor infiltrations because the second transgene within these constructs, GFP, displayed strong fluorescence that was significantly higher than background (p<0.0001). Thus, these results show that the de novo candidate regula- Example 4: *Agrobacterium*-mediated Transformation of *Arabidopsis* and Molecular Analyses of Transgenic Events

*Arabidopsis thaliana* ecotype Columbia-0 (Col-0) was used to test the relative expression of RFP/AAD12 reporter under the control of the GmCAB2 regulatory elements. A standard *Arabidopsis* transformation procedure was used to produce transgenic seed by inflorescence dip method (Clough and Bent, 1998). The $T_1$ seeds were sown on selection trays (10.5"×21"×1", T.O. Plastics Inc., Clearwater, Minn.). For this, 200 mg of cold stratified seeds (0.1% agar+385 mg/L Liberty for 48 hours before sowing) were distributed on selection trays using a modified air driven spray apparatus to distribute 10 ml of seed suspension per selection tray. Trays were covered with humidity domes, marked with seed identifier, and placed in a Conviron™ with an individual watering tray under each flat. The humidifying dome was removed approximately five days post-sowing. The first watering of selection trays was done using sub-irrigation with Hoagland's fertilizer at approximately 10-14 days post-sowing. In addition to stratification with the herbicide, plants are sprayed with a 0.2% solution (20 µl/10 mL distilled $H_2O$) of Liberty™ herbicide seven and nine days post-sowing. The $T_1$ plants resistant to Liberty™ were transplanted from selection trays into two inch pots and allowed to grow for seven to ten days before sampling for molecular analysis.

Next, DNA was extracted from leaves using an approximately 0.5 square centimeter of *Arabidopsis* leaf that was pinched off each plant. The samples were collected in a 96-well DNA extraction plate. Then 200 µl of extraction buffer was added to each well and tissue was disrupted with three mm stainless steel beads using a Kleko™ tissue pulverizer (three minutes on the maximum setting). After tissue maceration, DNA was isolated using the BioSprint 96 DNA Plant Kit™.

For qPCR, transgene copy number was assayed using hydrolysis probe designed to detect the pat and aad12 genes (Table 2). The *Arabidopsis* endogenous gene, AtTaftI15 (*Arabidopsis* Locus: AT4G31720), was used for normalization of DNA template concentration (Table 2). The qPCR was performed as follows: 10 µl of Probes Master Mix™ with a final concentration of 0.4 µM of each primer and 0.2 µM of each probe. The PCR cycles were performed using 95° C. for 10 min, followed by 40 amplification cycles (95° C. for 1 min, 60° C. for 40 sec, and 72° C. for 1 sec) and 40° C. for 1 sec. All qPCR assays were run in bi-plex format, with pat or aad12 assays paired with assay for the endogenous gene AtTaftI15. The cp scores, the point at which the florescence signal crosses the background threshold using the advanced relative quantification algorithm, based on the ΔΔCt method, (LightCycler® software release 1.5) were used to analyze the real time PCR data. All samples were then calibrated to a known hemizygous plant to obtain the transgene copy number. Up to 100 $T_1$ events that were identified as being resistant to Liberty™ were screened to identify one and two copy transgene events that were used for further analyses of transgene expression in $T_1$ transgenic plants.

TABLE 2

Primers and probes used for genotyping and zygosity analyses of *Arabidopsis* transgenic plants

| Oligo name | Oligo Sequence | Fluorophore label | Target gene |
|---|---|---|---|
| AtTafII15 F | SEQ ID NO: 13 GAGGATTAGGGTTT CAACGGAG | — | AtTafII15 |
| AtTafII15R | SEQ ID NO: 14 GAGAATTGAGCTGA GACGAGG | — | AtTafII15 |
| AtTafII15 Probe | SEQ ID NO: 15 AGAGAAGTTTCGAC GGATTTCGGGC | HEX | AtTafII15 |
| PAT A primer | SEQ ID NO: 16 ACAAGAGTGGATTGA TGATCTAGAGAGGT | — | PAT |
| PAT S primer | SEQ ID NO: 17 CTTTGATGCCTATGT GACACGTAAACAGT | — | PAT |
| PAT_AS probe | SEQ ID NO: 18 AGGGTGTTGTGGCTG GTATTGCTTACGCT | Cy5 | PAT |

TABLE 2-continued

Primers and probes used for genotyping and zygosity analyses of *Arabidopsis* transgenic plants

| Oligo name | Oligo Sequence | Fluorophore label | Target gene |
|---|---|---|---|
| AAD12 F | SEQ ID NO: 19 CAGAGTCCATGCTCA CCAAT | — | AAD12 |
| AAD12 R | SEQ ID NO: 20 ACGTGGCAACTTGAA ATCC | — | AAD12 |
| AAD12 Probe | SEQ ID NO: 21 TGGAGATGTGGTTGT GTGGGACAA | Cy5 (T1) or FAM (T2) | AAD12 |

Example 5: Evaluation of Genes Operably Linked to GmCAB2 Regulatory Sequences in $T_1$ *Arabidopsis* Plants To evaluate expression of the RFP/AAD12 reporter gene driven by the GmCAB2 promoter, GmCAB2 5' UTR and GmCAB2 terminator regulatory elements, single copy transgenic events were identified and assayed for RFP/AAD12 fluorescence using Typhoon instrument. All samples were scanned on three channels: chlorophyll (488 nm blue laser, 670 nm BP30, 580 nm split), GFP (488 nm blue laser, 520 nm BP40, 580 nm split), and RFP (532 nm green laser, 580 nm BP30). The PMT setting for leaf tissue was for chlorophyll 400, GFP 400 and RFP 420. For analyses of fluorescence in leaves, fully expanded rosette leaves from low copy (1-2 copies) transgenic events were harvested from each plant and scanned from adaxial (top) side. The "Contour Draw" function was used to outline leaf shapes and normalized fluorescence was determined by dividing signal volume by surface of the leaf. The results are shown in Table 3.

Analysis of the $T_1$ events for RFP/AAD12 fluorescence revealed that the GmCAB2 regulatory elements supported high mean RFP/AAD12 fluorescence (1825.1 pixels/area) that was statistically higher (p<0.0001) than the mean background fluorescence (350.5 pixels/area) detected in the non transgenic wild type control (Wt) (Table 3). These results show that the GmCAB2 regulatory sequences drove higher than background expression of the RFP/AAD12 reporter in transgenic *Arabidopsis thaliana* plants. The mean RFP/AAD12 fluorescence produced by the GmCAB2 regulatory elements was not statistically different from the RFP/AAD12 fluorescence levels of the pDAB117559 and pDAB117560 benchmark constructs (p=0.0912 and 0.1551, respectively, not shown). In the pDAB117559 and pDAB117560 constructs the RFP/AAD12 reporter was under the control of the following regulatory elements; *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator, respectively. Thus, pDAB122138 supported RFP/AAD12 fluorescence similar to that of the positive pDAB117559 and pDAB117560 controls, indicating that GmCAB2 is highly efficacious as regulatory sequence in *Arabidopsis* transgene applications. Based on the above results the transgenic pDAB122138 events containing the GmCAB2 regulatory sequences were advanced for further characterization in T2 *Arabidopsis*.

TABLE 3

Results of testing expression of RFP/AAD12 reporter gene/heterologous coding sequence expression in leaves of transgenic $T_1$ Arabidopsis plants

| Construct | Regulatory Element | No. of events | RFP fluorescence (pixels/area) | | | | GFP fluorescence (pixels/area) | | | |
|---|---|---|---|---|---|---|---|---|---|---|
| | | | Mean | Median | Std Dev | Std Err | Mean | Median | Std Dev | Std Err |
| Wt | None (Background) | 57 | 350.5 | 269.3 | 231.4 | 30.7 | 665.2 | 614.1 | 218.0 | 28.9 |
| pDAB 117559 | AtUbi14/AtUbi14 | 60 | 1492.3*** | 1537.3 | 495.2 | 63.9 | 5164.1*** | 5164.7 | 1605.8 | 207.3 |
| pDAB 117560 | AtUbi10/AtuOrf23 | 63 | 1547.6*** | 1556.1 | 504.5 | 63.6 | 5521.2*** | 5515.4 | 1434.3 | 180.7 |
| pDAB 122138 | GmCAB2/GmCAB2 | 20 | 1825.1*** | 1425.1 | 1485.9 | 796.2 | 7749.4*** | 6707.5 | 2378.4 | 531.8 |

Note:
***indicates means that are different from the mean of the mean fluorescence of the Wt control at $p < 0.0001$. Due to presence of unequal variances, Welch t-test was used to compare mean RFP or GFP fluorescence of each construct to the corresponding fluorescence means of Wt background control. Statistical analyses were conducted using JMP ® statistical package.

Example 6: Expression of Genes Operably Linked to GmCAB2 Regulatory Sequences in Leaves of $T_2$ Arabidopsis Plants The GmCAB2 regulatory sequences exhibited lower, but significantly higher than background, expression levels as compared to the expression levels of the benchmark *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator regulatory sequences in $T_1$ *Arabidopsis* (EX- AMPLE 5). Selected events that contained the GmCAB2 regulatory sequences driving the RFP/AAD12 reporter gene were advanced for further characterization in $T_2$ *Arabidopsis* plants. Accordingly, five $T_1$ plants that expressed from medium to high levels of RFP/AAD12 and GFP were selected. These five plants contained transgenic events of pDAB122138 and were used for T2 plant testing. From these five events, 56 plants were grown for each event. The T2 plants were molecularly genotyped as described in EXAMPLE 4. Based on molecular analyses, all homozygous and a comparable number of hemizygous plants were retained for fluorescence analysis of the four single copy events. To simplify data interpretation for the one two-copy transgenic event, only hemizygous plants were retained for expression analyses.

The results of analyses in T2 transgenic plants are provided in Table 4. The results for homozygous (1 copy) and hemizygous (1 and 2 copy) pDAB122138 transgenic plants that contained the RFP/AAD12 transgene under the control of GmCAB2 regulatory elements exhibited RFP/AAD12 fluorescence that was significantly higher than the background fluorescence from non transgenic control plants. The mean RFP/AAD12 fluorescence produced by hemizygous (7243.0 pixels/area) and homozygous (11340.2 pixels/area) for a transgene plants carrying the GmCAB2 regulatory elements was significantly higher than background fluorescence (1137.5 pixels/area, p<0.0001, Table 4). Comparing the hemizygous pDAB122138 plants to the hemizygous plants of the pDAB117559 and pDAB117560 benchmark constructs revealed that pDAB122138 supported RFP/AAD12 fluorescence that was lower than that of pDAB117559 (10943.2 pixels/area, p<0.0001) and was similar to that of pDAB117560 (8239.2 pixels/area, p=0.0965, not shown). Comparing the homozygous pDAB122138 plants to the homozygous plants of the pDAB117559 and pDAB117560 benchmark constructs revealed that pDAB122138 supported lower RFP/AAD12 fluorescence relatively both pDAB117559 (17194.3 pixels/area) and pDAB117560 (15334.3 pixels/area) benchmark constructs (p<0.0001, not shown). In the pDAB117559 and pDAB117560 constructs, the RFP/AAD12 reporter was under the control of the following regulatory elements; *Arabidopsis thaliana* Ubiquitin 14 promoter::*Arabidopsis thaliana* Ubiquitin 14 terminator, and the *Arabidopsis thaliana* Ubiquitin 10 promoter::*Agrobacterium tumefaciens* Orf23 terminator, respectively. These results demonstrate that the GmCAB2 regulatory sequences support the robust heritable expression of transgenes in two generations of transgenic events.

TABLE 4

Results of testing expression of RFP/AAD12 reporter gene/heterologous coding sequence expression in leaves of transgenic $T_2$ Arabidopsis plants

| Construct | Regulatory Elements | Zygocity | No. of plants | RFP fluorescence (pixels/area) | | | | GFP fluorescence (pixels/area) | | | |
|---|---|---|---|---|---|---|---|---|---|---|---|
| | | | | Mean | Median | Std Dev | Std Err | Mean | Median | Std Dev | Std Err |
| Wt | None (background) | none | 15 | 1137.5 | 1062.9 | 384.0 | 99.2 | 337.0 | 322.8 | 60.3 | 15.6 |
| pDAB 117559 | AtUbi14/AtUbi14 | hemi | 26 | 10943.2*** | 10394.5 | 2862.0 | 561.3 | 3352.3*** | 3355.0 | 380.2 | 74.6 |
| | | homo | 40 | 17194.3*** | 16208.0 | 6090.0 | 962.9 | 5649.3*** | 6144.2 | 1509.4 | 238.7 |
| pDAB 117560 | AtUbi10/AtuOrf23 | hemi | 25 | 8239.2*** | 8031.3 | 1928.4 | 385.7 | 3436.3*** | 3312.6 | 674.3 | 134.9 |
| | | homo | 50 | 15334.3*** | 15077.5 | 4080.2 | 577.0 | 6308.3*** | 6152.4 | 1385.5 | 195.9 |

TABLE 4-continued

Results of testing expression of RFP/AAD12 reporter gene/heterologous coding sequence expression in leaves of transgenic T₂ *Arabidopsis* plants

| Construct | Regulatory Elements | Zygocity | No. of plants | RFP fluorescence (pixels/area) | | | | GFP fluorescence (pixels/area) | | | |
|---|---|---|---|---|---|---|---|---|---|---|---|
| | | | | Mean | Median | Std Dev | Std Err | Mean | Median | Std Dev | Std Err |
| pDAB 122138 | GmCAB2/ | hemi | 25 | 7243.0*** | 7218.9 | 2215.8 | 443.2 | 5055.8*** | 4806 | 1950.84 | 390.2 |
| | GmCAB2 | homo | 37 | 11340.2*** | 10249.8 | 4703.8 | 773.3 | 7665.2*** | 6789.2 | 3708.7 | 609.7 |

Note:
***indicates means that are different from the mean of the mean fluorescence of the Wt control at p < 0.0001. Due to presence of unequal variances, Welch t-test was used to compare mean RFP or GFP fluorescence of each construct to the corresponding fluorescence means of Wt background control. Statistical analyses were conducted using JMP ® statistical package.

Interrogating the individual transgenic events (Table 5) revealed that RFP/AAD12 fluorescence detected in all examined independent transgenic events. In four single copy transgenic events, the homozygous plants exhibited higher average RFP/AAD12 fluorescence than the hemizygous plants indicating that transgene expression in these events was copy number dependent.

In summary, testing of the transgenic T2 *Arabidopsis* events showed that the GmCAB2 regulatory elements drive heritable expression of the RFP/AAD12 reporter gene that is higher than the Wt background. These results reaffirm that the GmCAB2 regulatory elements are effective in driving heritable transgene expression in stably transformed *Arabidopsis* plants.

Example 7: Other Transgenic Plants Produced with the GmCAB2 Regulatory Elements Soybean may be transformed with genes operably linked to the GmCAB2 promoter, the GmCAB2 5' UTR, the GmCAB2 3' UTR and/or the GmCAB2 terminator by utilizing the same techniques previously described in Example #11 or Example #13 of patent application WO 2007/053482.

Cotton may be transformed with genes operably linked to the GmCAB2 promoter, the GmCAB2 5' UTR, the GmCAB2 3' UTR and/or the GmCAB2 terminator by utilizing the same techniques previously described in Examples #14 of U.S. Pat. No. 7,838,733 or Example #12 of patent application WO 2007/053482 (Wright et al.).

TABLE 5

Results of testing expression of RFP/AAD12 reporter gene/heterologous coding sequence expression in leaves of homozygous and hemizygous plants of the individual T₂ *Arabidopsis* events

| Construct | Event | Regulatory Element name | Number of samples | RFP fluorescence (pixels/area) | | | | GFP fluorescence (pixels/area) | | | |
|---|---|---|---|---|---|---|---|---|---|---|---|
| | | | | Mean | Median | Std Dev | Std Err | Mean | Median | Std Dev | Std Err |
| Col-0 | Wt | none | 15 | 1137.5 | 1062.9 | 384.0 | 99.2 | 337.0 | 322.8 | 60.3 | 15.6 |
| pDAB117559; | 117559[2]-057 | hemi | 5 | 10415.0 | 10400.7 | 930.2 | 416.0 | 3529.5 | 3519.1 | 159.8 | 71.5 |
| AtUbi14/AtUbi14 | 117559[2]-057 | homo | 8 | 17840.7 | 19158.8 | 3743.1 | 1323.4 | 6196.5 | 6607.7 | 1257.6 | 444.6 |
| | 117559[2]-062 | hemi | 6 | 9320.9 | 9586.9 | 808.9 | 330.2 | 3486.9 | 3472.2 | 161.6 | 66.0 |
| | 117559[2]-062 | homo | 9 | 14534.0 | 16156.6 | 3679.1 | 1226.4 | 5455.1 | 6345.2 | 1482.7 | 494.2 |
| | 117559[8]-246 | hemi | 5 | 14037.8 | 13650.2 | 1112.2 | 497.4 | 3351.0 | 3316.9 | 488.5 | 218.4 |
| | 117559[8]-246 | homo | 9 | 23442.5 | 25126.5 | 5547.1 | 1849.0 | 5724.0 | 5870.9 | 1573.9 | 524.6 |
| | 117559[8]-314 | hemi | 5 | 13987.2 | 13806.8 | 1671.9 | 747.7 | 3411.0 | 3489.6 | 465.9 | 208.3 |
| | 117559[8]-314 | homo | 4 | 21176.8 | 20884.0 | 7321.8 | 3660.9 | 5296.8 | 5217.0 | 2391.4 | 1195.7 |
| | 117559[8]-391 | hemi | 5 | 7279.7 | 7364.9 | 922.8 | 412.7 | 2956.2 | 3020.1 | 350.4 | 156.7 |
| | 117559[8]-391 | homo | 10 | 11855.0 | 12938.5 | 2711.7 | 857.5 | 5459.9 | 5750.6 | 1475.0 | 466.4 |
| pDAB117560; | 117560[2]-191 | hemi | 5 | 8889.2 | 9549.1 | 2092.5 | 935.8 | 3831.1 | 4015.2 | 859.5 | 384.4 |
| AtUbi10/AtuOrf23 | 117560[2]-191 | homo | 10 | 15330.1 | 14866.4 | 4404.6 | 1392.9 | 6352.1 | 6030.2 | 1756.8 | 555.6 |
| | 117560[3]-254 | hemi | 5 | 9158.7 | 8167.0 | 2264.3 | 1012.6 | 3611.3 | 3358.9 | 664.3 | 297.1 |
| | 117560[3]-254 | homo | 10 | 14704.1 | 14959.2 | 4009.6 | 1267.9 | 6283.7 | 6343.9 | 1273.8 | 402.8 |
| | 117560[3]-288 | hemi | 5 | 6506.8 | 6287.3 | 948.7 | 424.3 | 3066.4 | 3136.1 | 256.9 | 114.9 |
| | 117560[3]-288 | homo | 10 | 18550.4 | 18921.9 | 3158.6 | 998.8 | 7007.3 | 6673.1 | 1175.3 | 371.7 |
| | 117560[3]-325 | hemi | 5 | 7716.5 | 6838.0 | 1951.7 | 872.8 | 3172.3 | 3092.6 | 668.9 | 299.1 |
| | 117560[3]-325 | homo | 10 | 14238.9 | 13152.0 | 4636.8 | 1466.3 | 6230.7 | 5924.0 | 1444.7 | 456.9 |
| | 117560[3]-353 | hemi | 5 | 8924.7 | 8444.1 | 1354.0 | 605.5 | 3503.5 | 3459.6 | 733.6 | 328.1 |
| | 117560[3]-353 | homo | 10 | 13848.3 | 13274.7 | 2821.9 | 892.4 | 5667.9 | 5782.0 | 1125.1 | 355.8 |
| pDAB122138; | 122138[2]-015 | hemi | 5 | 9839.0 | 9874.3 | 907.8 | 406.0 | 7051.1 | 7011.6 | 753.4 | 336.9 |
| GmCAB2/GmCAB2 | | homo | 10 | 14386.6 | 15350.7 | 4942.8 | 1563.1 | 11145.9 | 11939.7 | 3385.3 | 1070.5 |
| | 122138[3]-053 | hemi | 5 | 6722.5 | 6275.6 | 859.1 | 384.2 | 3412.6 | 3357.5 | 561.1 | 250.9 |
| | | homo | 10 | 9989.4 | 9933.0 | 3655.9 | 1156.1 | 4323.9 | 4147.5 | 1290.2 | 408.0 |
| | 122138[3]-056 | hemi | 5 | 4081.9 | 3675.5 | 897.8 | 401.5 | 2934.5 | 2985.6 | 636.8 | 284.8 |
| | | homo | 10 | 7667.6 | 7686.4 | 2039.4 | 644.9 | 6063.0 | 6432.8 | 1811.7 | 572.9 |
| | 122138[4]-144 (Two copy) | hemi | 5 | 7433.0 | 7218.9 | 888.3 | 397.3 | 6210.3 | 5962.3 | 1681.7 | 752.1 |
| | 122138[5]-189 | hemi | 5 | 8138.5 | 8171.1 | 1999.8 | 894.4 | 5670.4 | 5409.2 | 1613.6 | 721.6 |
| | | homo | 7 | 14164.2 | 12672.9 | 4418.9 | 1670.2 | 9755.1 | 11151.2 | 3120.8 | 1179.6 |

Canola may be transformed with genes operably linked to the GmCAB2 promoter, the GmCAB2 5' UTR, the GmCAB2 3' UTR and/or the GmCAB2 terminator by utilizing the same techniques previously described in Example #26 of U.S. Pat. No. 7,838,733 or Example #22 of patent application WO 2007/053482 (Wright et al.).

Wheat may be transformed with genes operably linked to the GmCAB2 promoter, the GmCAB2 5' UTR, the GmCAB2 3' UTR and/or the GmCAB2 terminator by utilizing the same techniques previously described in Example #23 of patent application WO 2013/116700A1 (Lira et al.).

Rice may be transformed with genes operably linked to the GmCAB2 promoter, the GmCAB2 5' UTR, the GmCAB2 3' UTR and/or the GmCAB2 terminator by utilizing the same techniques previously described in Example #19 of patent application WO 2013/116700A1 (Lira et al.).

Example 8: *Agrobacterium*-mediated Transformation of Genes Operably Linked to the GmCAB2 Regulatory Elements In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," *Plant Physiol.* 1997 November; 115(3):971-980. For *Agrobacterium*-mediated transformation of rice, see, e.g., Hiei et al., "Transformation of rice mediated by *Agrobacterium tumefaciens*," *Plant Mol. Biol.* 1997 September; 35(1-2):205-18.

The Latin names for these and other plants are given below. It should be clear that other (non *Agrobacterium*) transformation techniques can be used to transform genes operably linked to GmCAB2 promoter, the GmCAB2 5' UTR, the GmCAB2 3' UTR and/or the GmCAB2 terminator, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*). Transformation of such plants, with genes operably linked to the GmCAB2 promoter, the GmCAB2 5' UTR, the GmCAB2 3' UTR and/or the GmCAB2 terminator, for example, is contemplated in embodiments of the subject disclosure.

Use of the GmCAB2 promoter, the GmCAB2 5' UTR, the GmCAB2 3' UTR and/or the GmCAB2 terminator to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of GmCAB2 promoter, the GmCAB2 5' UTR, the GmCAB2 3' UTR and/or the GmCAB2 terminator to drive operably linked genes can be deployed in ornamental and fruit-bearing species. Such applications are also within the scope of embodiments of this disclosure. Examples include, but are not limited to; rose (Rosa spp.), burning bush (*Euonymus* spp.), petunia (*Petunia* spp.), begonia (*Begonia* spp.), rhododendron (*Rhododendron* spp.), crabapple or apple (*Malta* spp.), pear (*Pyrus* spp.), peach (*Prunus* spp.), and marigolds (*Tagetes* spp.).

Example 8: *Agrobacterium*-Mediated Transformation of Soybean (*Glycine max*) with Genes Operably Linked to the GmCAB2 Regulatory Elements To test the ability of GmCAB2 upstream regulatory sequences (promoter and 5'UTR) to drive transgene expression in soybean transgenic plants, a construct containing a variant of GmCAB2 gene promoter sequence (SEQ ID: NO:28; GmCAB2.1) and the GmCAB2 5' UTR sequence (SEQ ID NO:3), was paired with the terminator from the *Phaseolus vulgaris* Phaseolin gene (PvPhas). These regulatory sequences GmCAB2 promoter (SEQ ID NO:28) and GmCAB2 5'UTR (SEQ ID NO:3)/PvPhas terminator were fused to the coding sequence of an insecticidal protein denoted here as Insecticidal Protein A (IP-A). The resulting construct was stably integrated into the soybean genome using biolistic bombardment and FLP/FRT recombinase mediated cassette exchange (RMCE). RMCE relies on replacing the specific previously integrated in the soybean genome sequence with the donor sequence to generate independent transgenic events integrated in the same genomic location (see, Tao et al., (2007) Modified FRT recombination sites and methods of use, WO2007011733; and, Li et al., (2009) Site-Specific Integration of Transgenes in Soybean via Recombinase-Mediated DNA Cassette Exchange Plant Physiology, Vol. 151, pp. 1087-1095.). A control construct containing IP-A under the control of the *Arabidopsis* Ubiquitin10 promoter and 5'UTR and the Ubiquitin14 terminator (AtUbi10/AtUbi14) regulatory sequences was integrated in the same soybean genomic location as the test construct with the GmCAB2 promoter and 5'UTR (Tao et al., 2007, Li et al., 2009). All of the transformants also contained a selectable cassette that specifies resistance to chlorsulfuron (Tao et al., 2007, Li et al., 2009). The soybean plants resistant to chlorsulfuron were molecularly screened and events containing complete, single copy insertions were regenerated. Transgenic soybean plants were grown to maturity under typical greenhouse growth conditions. To assay transgenic protein accumulation levels, leaves of the T0 transgenic plants were sampled, protein was extracted, and protein accumulation of IP-A was determined using standard Western blotting technique. Results of these analyses are shown in Table 6. Statistical analyses of the IP-A protein levels revealed no statistically significant differences between the mean protein levels of the test construct and that in the control construct (p=0.7221). Therefore, these results in transgenic soybean plants demonstrate that GmCab2 promoter of SEQ ID NO:28 and 5'UTR of SEQ ID NO:3 support levels of protein comparable for that of the strong ubiquitous AtUbi10 promoter (Norris et al., (1993) The intron of *Arabidopsis thaliana* polyubiquitin genes is conserved in location and is a quantitative determinant of chimeric gene expression. Plant Mol Biol. March; 21(5): 895-906). Furthermore, in this experiment PvPhas terminator was paired with the GmCAB2 promoter of SEQ ID NO:28 upstream regulatory sequence, these results, therefore, show that the GmCAB2 promoter of SEQ ID NO:28 functions to drive robust expression of a heterologous coding sequence in combination with the heterologous downstream regulatory sequences in transgenic soybean plants.

TABLE 6

Accumulation of Insecticidal Protein A (IP-A) in leaves of T0 soybean transgenic plants

| | | Protein level (ppm) | | | | |
|---|---|---|---|---|---|---|
| Regulatory sequence | Event ID | Individual events | Mean | Median | StDev | StErr |
| GmCab2.1/PvPhas | 1 | 174 | 225 | 237.5 | 55 | 19 |
| | 2 | 146 | | | | |
| | 3 | 186 | | | | |
| | 4 | 251 | | | | |
| | 5 | 246 | | | | |
| | 6 | 231 | | | | |
| | 7 | 244 | | | | |
| | 8 | 322 | | | | |
| AtUbi10/AtUbi14 | 1 | 1200 | 383.9 | 180.5 | 370 | 117 |
| | 2 | 139 | | | | |
| | 3 | 55 | | | | |
| | 4 | 140 | | | | |
| | 5 | 513 | | | | |
| | 6 | 215 | | | | |
| | 7 | 102 | | | | |
| | 8 | 146 | | | | |
| | 9 | 638 | | | | |
| | 10 | 691 | | | | |

Notes:
[1] protein accumulation levels were normalized to the total soluble protein and expressed as parts per million (ppm). The ppm values were rounded to the closest interger. [2] No significant differences were detected between the control AtUbi10/AtUbi14 and GmCAB2.1/PvPhas constructs (p = 0.7221). Due to presence of unequal variances, nonparametric comparisons using Dunn method for joint ranks was used for analyses. Statistical analyses were conducted using JMP ® statistical package.

Example 9: GmCAB2 Promoter and 5'UTR Support Accumulation of Insecticidal Protein B (IP-B) in T1 Transgenic Soybean Plants To test the ability of GmCAB2 upstream regulatory sequences (promoter and 5'UTR) to drive heritable transgene expression in T1 soybean transgenic plants, a construct containing the variant version of GmCAB2 gene promoter sequence (SEQ ID: NO:28) and GmCAB 5'UTR (SEQ ID NO:3) was paired with OsT28 (Bhyri, P., Krishnamurthy, N., Narayamam, E., Nott, A., Sarangi, R. R. (2013) Novel Plant Terminator Sequences, WO2013122729 A2) terminator from the converging rice genes (LOC_Os03g60090.1 and LOC_Os03g60080.1). These regulatory sequences GmCAB2 (SEQ ID NO:28) promoter, 5'UTR (SEQ ID NO:3) and OsT28 terminator (GmCAB2/OsT28) were used to drive expression of the coding sequence of the IP-B insecticidal protein. Other genes present in the construct were an expression cassettes containing another insecticidal protein and an expression cassette containing the acetolactate synthase gene (Gm-HRA) conferring resistance to sulfonylurea herbicides ((Mazur, B. J. And Falco S. C. (1989) The development of herbicide restsnat crops. *Annu. Rev. Plant Phylsiol. Plant Mol. Biol.* 40:441; and Green J. M. (2007) Review of Glyphosate and Als-inhibiting Herbicide Crop Resistance and Resistant Weed Management Weed Technology 21(2):547-558)) that was used as a selectable marker during plant transformation. Transgenic T0 plants were produced from immature seed cultures following the *Agrobacterium*-mediated transformation protocol (Finer J J, McMullen M D (1991) Transformation of soybean via particle bombardment of embryogenic suspension culture tissue. Vitro Cell Dev Biol-Plant 27:175-182; Stewart C N Jr, Adang M J, All J N, Boerma H R, Cardineau G, Tucker D, Parrott W A (1996) Genetic transformation, recovery, and characterization of fertile soybean transgenic for a synthetic *Bacillus thuringiensis* cryIAc gene. Plant Physiol 112:121-129; Cho H, Castle L A, Klein™, Minh T, Moy Y (2015). Cultivation medium for *Agrobacterium*-mediated transformation of dicot plants. U.S. Pat. No. 8,962,328)). Briefly, immature seeds were harvested from soybean pods of plants grown in the greenhouse under standard conditions. Seeds were surface sterilized, immature cotyledons were aseptically excised and the cultures were maintained in 250 ml flasks containing 50 ml of liquid media on rotary shakers at 26 C under cool white fluorescent lights with a 16/8 h day/night photoperiod (Samoylov V M, Tucker D M, Thibaud-Nissen F, Parrott W A (1998) A liquid-medium-based protocol for rapid regeneration from embryogenic soybean cultures. Plant Cell Rep 18:49-54; and Cho et al., (2015)). An *Agrobacterium tumefaciens* strain modified to carry plasmids with genes of interest were used to transform the immature soybean cotyledons. Transgenic soybean events were selected and grown to maturity under typical greenhouse growth conditions.

To produce T1 transgenic plants, seeds from an intact single copy transgenic event were planted in a greenhouse and young seedlings were genotyped using standard molecular biology techniques to identify null, hemizygous and homozygous transgenic plants. For evaluation of protein accumulation levels, leaves from V3 and R3 growth stages and immature pods ~2.5-3 cm long were collected from hemizygous and homozygous transgenic plants. Samples were frozen on dry ice and stored in −80 C freezer until freeze dried, ground, and used for protein extraction. Protein extraction and analyses of protein levels were similar to that described by Xu X T, Owens M A. (2011) Multiplexed protein quantification in maize leaves by liquid chromatography coupled with tandem mass spectrometry: an alternative tool to immunoassays for target protein analysis in genetically engineered crops. J Agric Food Chem. 2011 Apr. 27; 59(8):3551-8. doi: 10.1021/jf104516r. Epub 2011 Mar. 9.)

Results of protein analyses are shown in Table 7. Analyses of protein levels revealed that hemizygous and homozygous plants accumulated IP-B protein int all assayed tissues; V3 and R3 leaves and immature pods. Comparing mean protein accumulation levels between the homozygous and hemizygous transgenic plants revealed that there was statistically higher protein levels in homozygous plants relative the hemizygous plants, and this was true for all tested tissues (Table 7). These results indicate that increased transgene copy number in the homozygous plants resulted in higher protein accumulation. Copy number-dependent IP-B protein accumulation in the V3 and R3 leaves and immature pods of the homozygous transgenic plants demonstrates that GmCAB2 promoter of SEQ ID NO:28 and 5'UTR of SEQ ID NO:3 support heritable and trans-generationally stable IP-B transgene expression. Furthermore, in this experiment GmCAB2 promoter/5'UTR of SEQ ID NO:28 and SEQ ID NO:3 were paired with the OsT28 terminator from the heterologous monocot species, rice. This suggests that GmCAB2 promoter functions to drive robust expression of a heterologous coding sequence in a combination with heterologous downstream transcription termination sequences from a dicot (Example 8) or a monocot (this example) plant species.

TABLE 7

Accumulation of IP-B protein in the V3 and R3 leaves and immature pods of T1 soybean plants

| Developmental stage[2] | Zygosity | Plant # | Protein level, ppm | Protein level (ppm)[1] | | | |
|---|---|---|---|---|---|---|---|
| | | | | Mean | Median | StdDev | StdErr |
| V3 leaf*** | Homozygous | 1 | 402 | 396 | 399 | 15 | 6 |
| | | 2 | 406 | | | | |
| | | 3 | 377 | | | | |
| | | 4 | 396 | | | | |
| | | 5 | 380 | | | | |
| | | 6 | 417 | | | | |
| | Hemizygous | 1 | 189 | 202 | 196 | 23 | 11 |
| | | 2 | 181 | | | | |
| | | 3 | 203 | | | | |
| | | 4 | 233 | | | | |
| R3 leaf** | Homozygous | 1 | 347 | 328 | 332 | 72 | 29 |
| | | 2 | 330 | | | | |
| | | 3 | 259 | | | | |
| | | 4 | 248 | | | | |
| | | 5 | 448 | | | | |
| | | 6 | 333 | | | | |
| | Hemizygous | 1 | 175 | 185 | 166 | 50 | 25 |
| | | 2 | 156 | | | | |
| | | 3 | 150 | | | | |
| | | 4 | 258 | | | | |
| Immature pods*** | Homozygous | 1 | 831 | 847 | 841 | 52 | 21 |
| | | 2 | 784 | | | | |
| | | 3 | 856 | | | | |
| | | 4 | 850 | | | | |
| | | 5 | 823 | | | | |
| | | 6 | 940 | | | | |
| | Hemizygous | 1 | 403 | 409 | 408 | 8 | 4 |
| | | 2 | 401 | | | | |
| | | 3 | 412 | | | | |
| | | 4 | 418 | | | | |

Notes:
[1]protein accumulation levels were normalized to the total soluble protein and expressed as parts per million (ppm). The ppm values were rounded to the nearest interger. [2]Significant differences between average protein levels of hemizygous and homozygous transgenic plants indicated by *<0.0001 and p = 0.0061. Statistical analyses were conducted using the Welch's Anova test in the JMP ® statistical package.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid vector comprising a promoter operably linked to a heterologous polynucleotide sequence of:
   a) a polylinker sequence;
   b) a non-GmCAB2 heterologous coding sequence; or
   c) a combination of a) and b);
   wherein said promoter comprises a polynucleotide sequence that has at least 95% sequence identity with SEQ ID NO:2.

2. The nucleic acid vector of claim 1, wherein said promoter is 1,299 bp in length.

3. The nucleic acid vector of claim 1, wherein said promoter consists of a polynucleotide sequence that has at least 95% sequence identity with SEQ ID NO:2.

4. The nucleic acid vector of claim 1, wherein said promoter is operably linked to a heterologous coding sequence.

5. The nucleic acid vector of claim 4, wherein the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein.

6. The nucleic acid vector of claim 1, further comprising a terminator polynucleotide sequence.

7. The nucleic acid vector of claim 1, further comprising a 3' untranslated polynucleotide sequence.

8. The nucleic acid vector of claim 1, further comprising a 5' untranslated polynucleotide sequence.

9. The nucleic acid vector of claim 1, further comprising an intron sequence.

10. The nucleic acid vector of claim 1, wherein said promoter has tissue preferred expression.

11. A transgenic plant comprising a promoter that has at least 95% sequence identity with SEQ ID NO:2 operably linked to a heterologous coding sequence.

12. The transgenic plant of claim 11, wherein said plant is selected from the group consisting of *Zea mays*, wheat, rice, sorghum, oats, rye, bananas, sugar cane, *Glycine max*, cotton, *Arabidopsis*, tobacco, sunflower, and canola.

13. The transgenic plant of claim 12, wherein said plant is *Glycine max*.

14. The transgenic plant of claim 11, wherein the heterologous coding sequence is inserted into the genome of said plant.

15. The transgenic plant of claim 11, further comprising a 3' untranslated sequence.

16. The transgenic plant of claim 11, wherein said heterologous coding sequence has tissue preferred expression.

17. The transgenic plant of claim 11, wherein said promoter is 1,299 bp in length.

18. A method for producing a transgenic plant cell, the method comprising the steps of:
 a) transforming a plant cell with a gene expression cassette comprising a GmCAB2 promoter, wherein said promoter comprises a polynucleotide sequence that has at least 95% sequence identity with SEQ ID NO:2, operably linked to at least one polynucleotide sequence of interest;
 b) isolating the transformed plant cell comprising the gene expression cassette; and,
 c) producing a transgenic plant cell comprising the GmCAB2 promoter of operably linked to at least one polynucleotide sequence of interest.

19. A method for expressing a polynucleotide sequence of interest in a plant cell, the method comprising introducing into the plant cell a polynucleotide sequence of interest operably linked to a GmCAB2 promoter, wherein said promoter comprises a polynucleotide sequence that has at least 95% sequence identity with SEQ ID NO:2.

* * * * *

SEQUENCE LISTING

```
<160> NUMBER OF SEQ ID NOS: 29

<210> SEQ ID NO 1
<211> LENGTH: 1981
<212> TYPE: DNA
<213> ORGANISM: Artificial Sequence
<220> FEATURE:
<223> OTHER INFORMATION: Synthetic GmCAB2  (promoter/5'UTR and
      terminator joined by multiple cloning site)

<400> SEQUENCE: 1
caaattcaaa caaacttaca tcccccgaaa gctttcaagt aagccgaagt gacctattag        60
cttcgttttt catgcttcca tgattaaaaa agtaattgca gaactccttc cagtatatga       120
gctcgaattg gggtgccaga tatgctaatt aattactttt atgatgcagg caagtgtgtt       180
ttcagatgct gttcgggatg atgttgattt ttataagtat gaactgcact cctttagctt       240
tgaagtttga tcactagtgg ataaattatt tatatcttga gctttgaaaa tcttccaatg       300
aaacttcatt cacactttct gtgaaaaata tcatctatta aagaatcttg tcgtggtcaa       360
tgctatgcat gacaacatat taactattta aaagataact taaaattata aatagttaca       420
tattataaaa tgctgtggtg gacatgttac cacttgtaga atttatatag taaaattgaa       480
tctataacaa cacgacactt tatgtttatg gaattgtcat gtatgtgata ataaataaga       540
ttaatgaaat tattataaaa aacaaggcct taatcgaaaa ttcaatatct ttctattttt       600
```

```
ttattttata  atagtaatat  aattaaggtg  ctttattttg  ttttctctta  attaccgtaa    660
ttctcattta  aatacaactt  ttctagctta  tgatattgaa  agttaattaa  aaaaccaata    720
acgtcctgaa  ttttaatcta  aaacttctag  tacgtttggt  ttcacatttt  agatataatt    780
tttaaaagtt  aatagttata  aatttgtatt  ttaaatgtga  ttttttttct  attttaatg     840 acttttaac   catgtacagt  tattcatact  gattttttaa  actgtttgct  tgaagagacc    900 gttttgaca   ccaagttaaa  gaggtcatta  tctcttctaa  aatcctaaga  tataatttcc    960
aaatgaaacc  aaatttgtaa  tgtagcgaag  atgagctgcc  acattgtgtt  cttgaggtcg   1020
aggcactact  agccctgtgt  ttctgtgtag  ttttactagc  aacacaagtt  ttttcttttt   1080
ttcaaaaata  aaaagaaag   aagaaaaaaa  atgtgatggg  tcactcacgg  gtttgcaatg   1140
ttagtgtagc  atcagcccaa  tccaaactat  cttccatacc  aatttccaag  ttttaattta   1200
aatttaaatt  tcttgactct  gttggacctg  aattgtgtgg  cttacattga  ccctctcgaa   1260
aacatctgag  gaagaagtct  ttgcatccac  gtggcagaat  aagagccact  atagcatgac   1320
aaaatatcag  catgagaatc  cacatccaaa  tccacgacca  atgaggtgtt  gctgagttgt   1380
gcatatcctc  atccacagta  tcatacgatc  ttctataaac  ctttgtagta  gctttcttca   1440
ttctccacaa  cacagaacaa  aaacaaagaa  aaaaaaaaac  ccttagccaa  cacaaccatc   1500
ggatccacac  gacaccatgg  tgagtagtta  gcttaatcac  ttaggtcacc  gagctcggat   1560
gcctacatgc  aatgcaatct  tctgctccct  tttgcagttc  ccttgtgttt  aactccattt   1620
tcactaatgt  aactcacact  gtgtagcaga  aaaatctgta  tgagaaccat  tatatttta    1680 tatattagaa  atttgggtcc  ccagaaaata  tcaactctta  cgtttggaat  tcaagttaac   1740
tagttcaaac  gttgaaacca  tgttcaagga  atctatctat  tagtgatgta  cgtgccttgt   1800
acaccatcca  attcaaagcc  atgattaaaa  ccataaacga  atgaatccat  cttccattac   1860
caacaacatc  caaagcccac  aaggccacaa  caagagaaag  agcaggcggg  cattcaatgt   1920
atccatctaa  atgcgtcaat  aatgtagtaa  gtcataagaa  aattaaaaaa  caaagaagtg   1980
a                                                                       1981
```

<210> SEQ ID NO 2
<211> LENGTH: 1299
<212> TYPE: DNA
<213> ORGANISM: Artificial Sequence
<220> FEATURE:
<223> OTHER INFORMATION: Synthetic GmCAB2 promoter

<400> SEQUENCE: 2

```
caaattcaaa  caaacttaca  tcccccgaaa  gctttcaagt  aagccgaagt  gacctattag    60
cttcgttttt  catgcttcca  tgattaaaaa  agtaattgca  gaactccttc  cagtatatga   120
gctcgaattg  gggtgccaga  tatgctaatt  aattactttt  atgatgcagg  caagtgtgtt   180
ttcagatgct  gttcgggatg  atgttgattt  ttataagtat  gaactgcact  cctttagctt   240
tgaagtttga  tcactagtgg  ataaattatt  tatatcttga  gctttgaaaa  tcttccaatg   300
aaacttcatt  cacactttct  gtgaaaaata  tcatctatta  aagaatcttg  tcgtggtcaa   360
tgctatgcat  gacaacatat  taactattta  aaagataact  taaaattata  aatagttaca   420
tattataaaa  tgctgtggtg  gacatgttac  cacttgtaga  atttatatag  taaaattgaa   480
tctataacaa  cacgacactt  tatgtttatg  gaattgtcat  gtatgtgata  ataaataaga   540
ttaatgaaat  tattataaaa  aacaaggcct  taatcgaaaa  ttcaatatct  ttctattttt   600
```

```
ttattttata atagtaatat aattaaggtg ctttattttg ttttctctta attaccgtaa      660
ttctcattta aatacaactt ttctagctta tgatattgaa agttaattaa aaaaccaata      720
acgtcctgaa ttttaatcta aaacttctag tacgtttggt ttcacatttt agatataatt     780
tttaaaagtt aatagttata aatttgtatt ttaaatgtga ttttttttct attttttaatg    840 acttttaac catgtacagt tattcatact gattttttaa actgtttgct tgaagagacc      900
gtttttgaca ccaagttaaa gaggtcatta tctcttctaa aatcctaaga tataatttcc     960
aaatgaaacc aaatttgtaa tgtagcgaag atgagctgcc acattgtgtt cttgaggtcg    1020
aggcactact agccctgtgt ttctgtgtag ttttactagc aacacaagtt ttttcttttt    1080
ttcaaaaata aaaagaaag aagaaaaaaa atgtgatggg tcactcacgg gtttgcaatg    1140
ttagtgtagc atcagcccaa tccaaactat cttccatacc aatttccaag ttttaattta    1200
aatttaaatt tcttgactct gttggacctg aattgtgtgg cttacattga ccctctcgaa    1260
aacatctgag gaagaagtct ttgcatccac gtggcagaa                          1299
```

<210> SEQ ID NO 3
<211> LENGTH: 124
<212> TYPE: DNA
<213> ORGANISM: Glycine max

<400> SEQUENCE: 3

```
ttgtgcatat cctcatccac agtatcatac gatcttctat aaacctttgt agtagctttc     60
ttcattctcc acaacacaga acaaaaacaa agaaaaaaaa aaacccttag ccaacacaac    120
catc                                                                 124
```

<210> SEQ ID NO 4
<211> LENGTH: 279
<212> TYPE: DNA
<213> ORGANISM: Glycine max

<400> SEQUENCE: 4

```
ggatgcctac atgcaatgca atcttctgct ccctttttgca gttcccttgt gtttaactcc     60
attttcacta atgtaactac acctgtgtag cagaaaaatc tgtatgagaa ccattatatt    120
tttatatatt agaaatttgg gtccccagaa aatatcaact cttacgtttg gaattcaagt    180
taactagttc aaacgttgaa accatgttca aggaatctat ctattagtga tgtacgtgcc    240
ttgtacacca tccaattcaa agccatgatt aaaaccata                           279
```

<210> SEQ ID NO 5
<211> LENGTH: 425
<212> TYPE: DNA
<213> ORGANISM: Glycine max

<400> SEQUENCE: 5

```
ggatgcctac atgcaatgca atcttctgct ccctttttgca gttcccttgt gtttaactcc     60
attttcacta atgtaactac acctgtgtag cagaaaaatc tgtatgagaa ccattatatt    120
tttatatatt agaaatttgg gtccccagaa aatatcaact cttacgtttg gaattcaagt    180
taactagttc aaacgttgaa accatgttca aggaatctat ctattagtga tgtacgtgcc    240
ttgtacacca tccaattcaa agccatgatt aaaaccataa acgaatgaat ccatcttcca    300
ttaccaacaa catccaaagc ccacaaggcc acaacaagag aaagagcagg cgggcattca    360
atgtatccat ctaaatgcgt caataatgta gtaagtcata agaaaattaa aaaacaaaga    420
agtga                                                                425
```

<210> SEQ ID NO 6
<211> LENGTH: 1416
<212> TYPE: DNA
<213> ORGANISM: Artificial Sequence
<220> FEATURE:
<223> OTHER INFORMATION: Synthetic GmAct7-2 promoter and 5'UTR from Glyma06g15520

<400> SEQUENCE: 6

```
aacaccagta tgacgaggtc gaccaacaat actgggaaac acagccctag gagcatcgtc      60
acagcaaatc ctgcctgtac acagatgatc atttaaataa attgagcaat aatgaaacca     120
agactaaata gatgcaatta cactaacaag aaactgcaaa gtactaacct tcaccattcc     180
agttccattg tcacaaacaa ggggttgaat atcctcagca tcagccattt tttaccaaac     240
tacagtacgc atacaataaa ttgtcagtac caccaagttt gaatagacaa tctacagaac     300
ccagccattt acagactttg agggtttact tcaaactctc tttttctaca caagacagca     360
tcatagtata taacacac aaaatcaata ggaaagaaaa caaggaaaaa aaataattca       420
gtattataca atctacttag aaataaaaca gtaacaaatg tacataaaca gataaaggag     480
ccgatcctgt gcattttta aatgaaactg ccaaaattaa tagatgaata gaaacgtcc       540
attaggacac cagctaaaat ctcagaagtc ctctgacaca gcatatctta agttcccaaa     600
ccaaatgatc ttctactaag aaagatcaat gaggaaaaaa ataaagccaa aaagtgata     660
aaaaaaacag atcagaccat aaatccatcc aacaccagat tatgtaatcg atggctatcc     720
acatttcaga ataagtaaag gtacagttca aaaagttcga agatctctgc tatagaagat     780
cggaactgtg atatgtcatt tccaccacta aaactacaga tcgccacaat ctactacatt     840
tcattcagta tagatcaggt agtacgaata taaataatca gatacaaaac atccagatat     900
gattttgatg aggtaggtaa caatcttatc tcacacagat ttaaaagaa aaacataaaa     960
aagagtacta ctatggaaca aatctaagaa taaacattcg agattgcaaa aagcgctgaa    1020
tcaaagagca aaaggaaacg tactttgcat caaagttatg atgtgagaga ttaagatgaa    1080
taccttgtgt gagaagaaga agatggctta gcactcactc acacacacac acactctctc    1140
tctctccggt gcttgagggc tacagaaaga ggaaagagga atgagaagag agaagggag    1200
aaggagaggg ggtatatata tgcggaaaga gagagtgtgt cgttggtgtg agagtgagag    1260
tgtaatgtaa tgtatttgaa attggaattg aggttgggac caaaaattga aattgaagga    1320
ctggagagag agggaatcat ttcgaccacg agaaaagagg gataggtga ctggatgaca     1380
gcctttcctt tttcatttca caccttcta cccttt                               1416
```

<210> SEQ ID NO 7
<211> LENGTH: 1686
<212> TYPE: DNA
<213> ORGANISM: Artificial Sequence
<220> FEATURE:
<223> OTHER INFORMATION: Synthetic GmGAPC2 promoter and 5' UTR from Glyma0618110

<400> SEQUENCE: 7

```
tcaaaccaag gcagcaccct cagtttctgg gcgtccagcg agtctggagt gccacatcac      60
acgtggcaac ttgaaatccc agggctcagc acggtggagc aaacagcggt tgtcccacac     120
aaccacatct ccagcagccc attggtgagc atggactctg ggagcctggc aggcccagtc     180
aacaagtcct tcaaggaagc gctctgattc agctgcatcc atgccaggga tggcatgggc     240
```

```
atggcggccg atcaagaggc tgggccttcc agtctcagga tgcaccttga ccaatggtct    300
gagaggagtt gcagtggtgt ccatgccata acctatgtag gctgacccgg cctgttggac    360
atgtcccaac ttgctctgag aatacacaag ggagtgacga gcagaccttt ggtgaacaag    420
agcacgggtt gcctcatcaa gggcatcgta ggctgccctc atgtcagcaa agcaggttct    480
gcccccaact gctgggacaa cttctgcgct gaacacagct ccttgagcca tgactggcat    540
gtaggttgag tcggcgtgcc aggccatgtt gcccacaatg accttcatca tgtcatccca    600
ctcagcagga gagtgctggc gcactgtgcc atctgccttg acattggata tggcaacaat    660
gtcacctccg ccaatcctct caattgctcc aaagcgttta gcaaaggtaa tctgttggtc    720
attgctgagg tgttgcccag ggaagatcaa gagtgcatgt tgaagccagg ctgcatggag    780
ggcagcgaaa ccagcatcgt caagtgtggc aaggtgaaca ccagtgactg tggcacccaa    840
ggtggcacca gtgggtgtga tttggagagt ggtctgagcc atggcagctg ccttagctgc    900
ggcttctttt gcggcagcct cctttgcagc ggcttccttg gctgcagcct ctttagcggc    960
tgcttcctcg gcgagattca acttgtgtcc gagcttgctg gaaggtcac agtaacgagc    1020 aacagccacc tcatgctgtt cgacataggt ttccttgtct gcctccttga tcctttccaa    1080
gcgatgatcc acatagtaga cgccaggcat cttgagattc ttagcaggtt tctttgagcg    1140
gtatgtggtc ttgaagttgc aaatcaaatg gccacctcca accaacttga gtgccatatc    1200
agacctcccc tcaagcccac catcggctgg gtaaagcatc tcggtgtttg cttcccatcc    1260
aagggttttc ttctgcataa ctggtccatt tgatggaaag ttcacacctc taatcttgac    1320
attgtagatg agacacccat cttgcaaaga agtgtcttga gtagcggtca acacgccacc    1380
atcttcgtaa gttgtaacac gctcccatgt gaaaccctca ggaaaagact gcttaaagaa    1440
gtcgggaatc ccttgtgtgt gattgatgaa agttctggag ccatacatga agctagtggc    1500
aagtatgtcg aaggcaaatg ggagtggtcc accctcaacc actttgatcc tcatggtctg    1560
ggttccctca taaggcttgc cttctcccte ggatgtgcat ttgaagtgat gattgttgac    1620
agtgccctcc atgtagagct tcatgtgcat gttctctttg ataagttcct cgcctttgct    1680
caccat                                                               1686

<210> SEQ ID NO 8
<211> LENGTH: 632
<212> TYPE: DNA
<213> ORGANISM: Glycine max

<400> SEQUENCE: 8
acaatattct tttcattcat atatcgtgta tccactaggt ttgaatgtaa aattattctt     60
gttatctgaa attcttgtga aattatttac tcaactaaaa acataacacg taacagagca    120
taatcataca cattaataaa ctcaatacta aaaatatta aaattaaatt taaccgatag     180
caaaattaga gtatttagat attttccctt cccttggact cctggtaaac cagggatcgt    240
gcaggtatcc tcaccattac aacttttaag tgtgtcttca tgcctatagc acactcaaat    300
atcgggcaag tgattcatga ataaactaaa atttgataat ttgagtgcga actgacaatc    360
ttatataaaa ttctcgatac atgtagctat agacattcac attaatgttc gaaggccaa     420 aaaaaatgtg aactctgaaa aaggatacat agaaaataaa ataagcattc acaatcactc    480
ctttgctaca gacaacctac tttcgaagac attgatgaat tccaaggtga aaatgcttc     540 tcatcaattc tgtgcccgcc acatccagag ggatgccaca caatatatga tacatcacag    600
ctccgaatat accctccaat cctatcccac ct                                  632
```

<210> SEQ ID NO 9
<211> LENGTH: 525
<212> TYPE: DNA
<213> ORGANISM: Glycine max

<400> SEQUENCE: 9

```
cgtttatcta gaacttcacg gaataatcag tttccaaaaa gtactttcac actattacag    60
tataacttat ccaaccaatt aagttttgaa tatcaggtac gccaatcaaa ccaatatgaa   120
ctaaaagcca aaatgttaa tttaaatacg gactaaaata agcacagaaa atgtttaaa    180
ccacgaatcc aagattcaaa gcaaacagga tcaaatatac gagaaccaca atgaaaaaa   240
aggacggaca atatctact ataacaatca ataacaagta cattagcaag tattcaagcc   300
aagtacatca gcgagtatat aaaaatccaa aaactcgatc cccctccaca agagaaaaca   360
tcaaaagtcc aaaaaagagc taatgctcct ccaacaagta acaccactgg tttcagaaac   420
cgatttattc agacctctca ttttttgctc gagcaagaca ctaaatcgca gctaaacata   480
aacatacggt aataatgtga agacaagcta ctttgaagta acacc                   525
```

<210> SEQ ID NO 10
<211> LENGTH: 1686
<212> TYPE: DNA
<213> ORGANISM: Artificial Sequence
<220> FEATURE:
<223> OTHER INFORMATION: The coding sequence of the chimeric RFP/AAD12 reporter gene

<400> SEQUENCE: 10

```
atggtgagca aggcgagga acttatcaaa gagaacatgc acatgaagct ctacatggag    60
ggcactgtca acaatcatca cttcaaatgc acatccgagg agaaggcaa gccttatgag   120
ggaacccaga ccatgaggat caaagtggtt gagggtggac cactcccatt tgccttcgac   180
atacttgcca ctagcttcat gtatggctcc agaactttca tcaatcacac acaagggatt   240
cccgacttct ttaagcagtc ttttcctgag ggtttcacat gggagcgtgt tacaacttac   300
gaagatggtg gcgtgttgac cgctactcaa gacacttctt tgcaagatgg tgtctcatc   360
tacaatgtca agattagagg tgtgaacttt ccatcaaatg gaccagttat gcagaagaaa   420
acccttggat gggaagcaaa caccgagatg ctttacccag ccgatggtgg gcttgagggg   480
aggtctgata tggcactcaa gttggttgga ggtggccatt tgatttgcaa cttcaagacc   540
acataccgct caaagaaacc tgctaagaat ctcaagatgc ctggcgtcta ctatgtggat   600
catcgcttgg aaaggatcaa ggaggcagac aaggaaacct atgtcgaaca gcatgaggtg   660
gctgttgctc gttactgtga ccttcccagc aagctcggac acaagttgaa tctcgccgag   720
gaagcagccg ctaagaggc tgcagccaag gaagccgctg caaggaggc tgccgcaaaa   780
gaagccgcag ctaaggcagc tgccatggct cagaccactc tccaaatcac acccactggt   840
gccaccttgg gtgccacagt cactggtgtt caccttgcca cacttgacga tgctggtttc   900
gctgccctcc atgcagcctg gcttcaacat gcactcttga tcttccctgg caacacctc   960
agcaatgacc aacagattac ctttgctaaa cgctttggag caattgagag gattggcgga  1020
ggtgacattg ttgccatatc caatgtcaag gcagatggca cagtgcgcca gcactctcct  1080
gctgagtggg atgacatgat gaaggtcatt gtgggcaaca tggcctggca cgccgactca  1140
acctacatgc cagtcatggc tcaaggagct gtgttcagcg cagaagttgt cccagcagtt  1200
gggggcagaa cctgctttgc tgacatgagg gcagcctacg atgcccttga tgaggcaacc  1260
```

```
cgtgctcttg ttcaccaaag gtctgctcgt cactcccttg tgtattctca gagcaagttg    1320
ggacatgtcc aacaggccgg gtcagcctac ataggttatg gcatggacac cactgcaact    1380
cctctcagac cattggtcaa ggtgcatcct gagactggaa ggcccagcct cttgatcggc    1440
cgccatgccc atgccatccc tggcatggat gcagctgaat cagagcgctt ccttgaagga    1500
cttgttgact gggcctgcca ggctcccaga gtccatgctc accaatgggc tgctggagat    1560
gtggttgtgt gggacaaccg ctgtttgctc caccgtgctg agccctggga tttcaagttg    1620
ccacgtgtga tgtggcactc cagactcgct ggacgcccag aaactgaggg tgctgccttg    1680
gtttga                                                              1686

<210> SEQ ID NO 11
<211> LENGTH: 3661
<212> TYPE: DNA
<213> ORGANISM: Artificial Sequence
<220> FEATURE:
<223> OTHER INFORMATION: Gene expression casette containing the GmCAB2
      promoter - GmCAB2 5' UTR - RFP/AAD12 coding sequence - GmCAB2
      terminator

<400> SEQUENCE: 11
caaattcaaa caaacttaca tcccccgaaa gctttcaagt aagccgaagt gacctattag      60
cttcgttttt catgcttcca tgattaaaaa agtaattgca gaactccttc cagtatatga     120
gctcgaattg gggtgccaga tatgctaatt aattactttt atgatgcagg caagtgtgtt     180
ttcagatgct gttcgggatg atgttgattt ttataagtat gaactgcact cctttagctt     240
tgaagtttga tcactagtgg ataaattatt tatatcttga gctttgaaaa tcttccaatg     300
aaacttcatt cacactttct gtgaaaaata tcatctatta aagaatcttg tcgtggtcaa     360
tgctatgcat gacaacatat taactattta aaagataact taaaattata aatagttaca     420
tattataaaa tgctgtggtg gacatgttac cacttgtaga atttatatag taaaattgaa     480
tctataacaa cacgacactt tatgtttatg gaattgtcat gtatgtgata ataaataaga     540
ttaatgaaat tattataaaa aacaaggcct taatcgaaaa ttcaatatct ttctattttt     600
ttattttata atagtaatat aattaaggtg ctttatttttg ttttctctta attaccgtaa     660
ttctcattta aatacaactt ttctagctta tgatattgaa agttaattaa aaaaccaata     720
acgtcctgaa ttttaatcta aaacttctag tacgtttggt ttcacatttt agatataatt     780
tttaaaagtt aatagttata aatttgtatt ttaaatgtga ttttttttct attttttaatg     840 acttttttaac catgtacagt tattcatact gattttttaa actgtttgct tgaagagacc     900
gtttttgaca ccaagttaaa gaggtcatta tctcttctaa aatcctaaga taaatttcc      960 aaatgaaacc aaatttgtaa tgtagcgaag atgagctgcc acattgtgtt cttgaggtcg    1020
aggcactact agccctgtgt ttctgtgtag ttttactagc aacacaagtt ttttcttttt    1080
ttcaaaaata aaaagaaag aagaaaaaaa atgtgatggg tcactcacgg gtttgcaatg    1140
ttagtgtagc atcagcccaa tccaaactat cttccatacc aatttccaag ttttaattta    1200
aatttaaatt tcttgactct gttggacctg aattgtgtgg cttacattga ccctctcgaa    1260
aacatctgag gaagaagtct ttgcatccac gtggcagaat aagagccact atagcatgac    1320
aaaatatcag catgagaatc cacatccaaa tccacgacca atgaggtgtt gctgagttgt    1380
gcatatcctc atccacagta tcatacgatc ttctataaac ctttgtagta gctttcttca    1440
ttctccacaa cacagaacaa aaacaaagaa aaaaaaaaac ccttagccaa cacaaccatc    1500
```

```
ggatccaaac aatggtgagc aaaggcgagg aacttatcaa agagaacatg cacatgaagc    1560
tctacatgga gggcactgtc aacaatcatc acttcaaatg cacatccgag ggagaaggca    1620
agccttatga gggaacccag accatgagga tcaaagtggt tgagggtgga ccactcccat    1680
ttgccttcga catacttgcc actagcttca tgtatggctc cagaactttc atcaatcaca    1740
cacaagggat tcccgacttc tttaagcagt cttttcctga gggtttcaca tgggagcgtg    1800
ttacaactta cgaagatggt ggcgtgttga ccgctactca agacacttct ttgcaagatg    1860
ggtgtctcat ctacaatgtc aagattagag gtgtgaactt tccatcaaat ggaccagtta    1920
tgcagaagaa aacccttgga tgggaagcaa acaccgagat gctttaccca gccgatggtg    1980
ggcttgaggg gaggtctgat atggcactca agttggttgg aggtggccat ttgatttgca    2040
acttcaagac acataccgc tcaaagaaac ctgctaagaa tctcaagatg cctggcgtct    2100
actatgtgga tcatcgcttg gaaaggatca aggaggcaga caaggaaacc tatgtcgaac    2160
agcatgaggt ggctgttgct cgttactgtg accttcccag caagctcgga cacaagttga    2220
atctcgccga ggaagcagcc gctaaagagg ctgcagccaa ggaagccgct gcaaaggagg    2280
ctgccgcaaa agaagccgca gctaaggcag ctgccatggc tcagaccact ctccaaatca    2340
cacccactgg tgccaccttg ggtgccacag tcactggtgt tcaccttgcc acacttgacg    2400
atgctggttt cgctgccctc catgcagcct ggcttcaaca tgcactcttg atcttccctg    2460
ggcaacacct cagcaatgac caacagatta cctttgctaa acgctttgga gcaattgaga    2520
ggattggcgg aggtgacatt gttgccatat ccaatgtcaa ggcagatggc acagtgcgcc    2580
agcactctcc tgctgagtgg gatgacatga tgaaggtcat tgtgggcaac atggcctggc    2640
acgccgactc aacctacatg ccagtcatgg ctcaaggagc tgtgttcagc gcagaagttg    2700
tcccagcagt tgggggcaga acctgctttg ctgacatgag ggcagcctac gatgcccttg    2760
atgaggcaac ccgtgctctt gttcaccaaa ggtctgctcg tcactccctt gtgtattctc    2820
agagcaagtt gggacatgtc caacaggccg ggtcagccta cataggttat ggcatgggaca    2880 ccactgcaac tcctctcaga ccattggtca aggtgcatcc tgagactgga aggcccagcc    2940
tcttgatcgg ccgccatgcc catgccatcc ctggcatgga tgcagctgaa tcagagcgct    3000
tccttgaagg acttgttgac tgggcctgcc aggctcccag agtccatgct caccaatggg    3060
ctgctggaga tgtggttgtg tgggacaacc gctgtttgct ccaccgtgct gagccctggg    3120
atttcaagtt gccacgtgtg atgtggcact ccagactcgc tggacgccca gaaactgagg    3180
gtgctgcctt ggtttgagta gttagcttaa tcacctagag ctcggtcacc gagctcggat    3240
gcctacatgc aatgcaatct tctgctccct tttgcagttc ccttgtgttt aactccattt    3300
tcactaatgt aactacacct gtgtagcaga aaaatctgta tgagaaccat tatattttta    3360
tatattagaa atttgggtcc ccagaaaata tcaactctta cgtttggaat tcaagttaac    3420
tagttcaaac gttgaaacca tgttcaagga atctatctat tagtgatgta cgtgccttgt    3480
acaccatcca attcaaagcc atgattaaaa ccataaacga atgaatccat cttccattac    3540
caacaacatc caaagcccac aaggccacaa caagagaaag agcaggcggg cattcaatgt    3600
atccatctaa atgcgtcaat aatgtagtaa gtcataagaa aattaaaaaa caaagaagtg    3660
a                                                                   3661

<210> SEQ ID NO 12
<211> LENGTH: 4584
<212> TYPE: DNA
<213> ORGANISM: Artificial Sequence
```

<220> FEATURE:
<223> OTHER INFORMATION: Gene expression cassette containing the GFP and PAT reporter/selectable marker genes

<400> SEQUENCE: 12

```
gtcgacctgc aggtcaacgg atcaggatat tcttgtttaa gatgttgaac tctatggagg      60
tttgtatgaa ctgatgatct aggaccggat aagttcccct cttcatagcg aacttattca     120
aagaatgttt tgtgtatcat tcttgttaca ttgttattaa tgaaaaaata ttattggtca     180
ttggactgaa cacgagtgtt aaatatggac caggccccaa ataagatcca ttgatatatg     240
aattaaataa caagaataaa tcgagtcacc aaaccacttg cctttttaa cgagacttgt      300
tcaccaactt gatacaaaag tcattatcct atgcaaatca ataatcatac aaaaatatcc     360
aataacacta aaaattaaa agaaatggat aatttcacaa tatgttatac gataaagaag      420
ttacttttcc aagaaattca ctgattttat aagcccactt gcattagata aatggcaaaa     480
aaaaacaaaa aggaaaagaa ataaagcacg aagaattcta gaaaatacga aatacgcttc     540
aatgcagtgg gacccacggt tcaattattg ccaattttca gctccaccgt atatttaaaa     600
aataaaacga taatgctaaa aaaatataaa tcgtaacgat cgttaaatct caacggctgg     660
atcttatgac gaccgttaga aattgtggtt gtcgacgagt cagtaataaa cggcgtcaaa     720
gtggttgcag ccggcacaca cgagtcgtgt ttatcaactc aaagcacaaa tacttttcct     780
caacctaaaa ataaggcaat tagccaaaaa caactttgcg tgtaaacaac gctcaataca     840
cgtgtcattt tattattagc tattgcttca ccgccttagc tttctcgtga cctagtcgtc     900
ctcgtctttt cttcttcttc ttctataaaa caatacccaa agcttcttct tcacaattca     960
gatttcaatt tctcaaaatc ttaaaaactt tctctcaatt ctctctaccg tgatcaaggt    1020
aaatttctgt gttccttatt ctctcaaaat cttcgatttt gttttcgttc gatcccaatt    1080
tcgtatatgt tctttggttt agattctgtt aatcttagat cgaagacgat tttctgggtt    1140
tgatcgttag atatcatctt aattctcgat tagggtttca taaatatcat ccgatttgtt    1200
caaataattt gagttttgtc gaataattac tcttcgattt gtgatttcta tctagatctg    1260
gtgttagttt ctagtttgtg cgatcgaatt tgtcgattaa tctgagtttt tctgattaac    1320
agagatctcc atggctcctg ccatgaagat tgaatgccgc atcactggca ccctcaacgg    1380
tgtggagttt gaattggttg gaggtggaga gggcacacct gaacaaggga ggatgaccaa    1440
caagatgaag tcaactaaag gggctctcac cttcagccca tacttgcttt ctcatgtcat    1500
gggctatgga ttctaccact ttggcaccta cccctctgga tatgagaacc ctttccttca    1560
tgccatcaac aatggaggct acacaaacac cagaattgag aagtacgaag atggtggagt    1620
cttgcatgtc tccttcagct accgctatga ggctgggagg gtcataggag acttcaaagt    1680
tgtgggcact ggattcccag aggactcagt catcttcact gacaagatca taggagcaa     1740
tgccactgtt gagcacctcc atccaatggg tgacaatgtg cttgttggtt catttgcacg    1800
taccttcagc ctcagagatg gtggctacta ttcctttgtg gttgattctc acatgcactt    1860
caaatctgca atccacccct ccatcctcca gaatgggggt ccaatgtttg ctttcagacg    1920
tgtggaagag ttgcacagca acacagaact tggcattgtg gagtaccagc atgccttcaa    1980
gacacccatt gcatttgctt gagtagttag cttaatcact taggtcacca gcataatttt    2040
tattaatgta ctaaattact gttttgttaa atgcaatttt gctttctcgg gatttaata    2100
tcaaaatcta tttagaaata cacaatattt tgttgcaggc ttgctggaga atcgatctgc    2160
tatcataaaa attacaaaaa aatttatttt gcctcaatta ttttaggatt ggtattaagg    2220
```

```
acgcttaaat tatttgtcgg gtcactacgc atcattgtga ttgagaagat cagcgatacg    2280
aaatattcgt agtactatcg ataatttatt tgaaaattca taagaaaagc aaacgttaca    2340
tgaattgatg aaacaataca aagacagata aagccacgca catttaggat attggccgag    2400
attactgaat attgagtaag atcacggaat ttctgacagg agcatgtctt caattcagcc    2460
caaatggcag ttgaaatact caaaccgccc catatgcagg agcggatcat tcattgtttg    2520
tttggttgcc tttgccaaca tgggagtcca aggttgcggc cgcttaatta acttactagt    2580
gctagcctcg aggtcgactc tgatcatgga tgctacgtca cggcagtaca ggactatcat    2640
cttgaaagtc gattgagcat cgaaacccag ctttcttgta caaagtggtt gcggccgctt    2700
aattaaattt aaatgtttgg gaagctaggc caccgtggcc cgcctgcagg ggaagcttgt    2760
ttaaacccag aaggtaatta tccaagatgt agcatcaaga atccaatgtt tacgggaaaa    2820
actatggaag tattatgtaa gctcagcaag aagcagatca atatgcggca catatgcaac    2880
ctatgttcaa aaatgaagaa tgtacagata caagatccta tactgccaga atacgaagaa    2940
gaatacgtag aaattgaaaa agaagaacca ggcgaagaaa agaatcttga agacgtaagc    3000
actgacgaca acaatgaaaa gaagaagata aggtcggtga ttgtgaaaga gacatagagg    3060
acacatgtaa ggtggaaaat gtaagggcgg aaagtaacct tatcacaaag gaatcttatc    3120
ccccactact tatccttta tattttccg tgtcatttt gcccttgagt tttcctatat    3180
aaggaaccaa gttcggcatt tgtgaaaaca agaaaaaatt tggtgtaagc tattttcttt    3240
gaagtactga ggatacaact tcagagaaat ttgtaagttt gtagatctcc atgtctccgg    3300
agaggagacc agttgagatt aggccagcta cagcagctga tatggccgcg gtttgtgata    3360
tcgttaacca ttacattgag acgtctacag tgaactttag gacagagcca caaacaccac    3420
aagagtggat tgatgatcta gagaggttgc aagatagata cccttggttg gttgctgagg    3480
ttgagggtgt tgtggctggt attgcttacg ctgggccctg gaaggctagg aacgcttacg    3540
attggacagt tgagagtact gtttacgtgt cacataggca tcaaaggttg ggcctaggat    3600
ccacattgta cacacatttg cttaagtcta tggaggcgca aggttttaag tctgtggttg    3660
ctgttatagg ccttccaaac gatccatctg ttaggttgca tgaggctttg ggatacacag    3720
cccgtggtac attgcgcgca gctggataca agcatggtgg atggcatgat gttggttttt    3780
ggcaaaggga ttttgagttg ccagctcctc caaggccagt taggccagtt acccagatct    3840
gactgagctt gagcttatga gcttatgagc ttagagctca gatcggcggc aatagcttct    3900
tagcgccatc ccgggttgat cctatctgtg ttgaaatagt tgcggtgggc aaggctctct    3960
ttcagaaaga caggcggcca aaggaaccca aggtgaggtg ggctatggct ctcagttcct    4020
tgtggaagcg cttggtctaa ggtgcagagg tgttagcggg gatgaagcaa aagtgtccga    4080
ttgtaacaag atatgttgat cctacgtaag gatattaaag tatgtattca tcactaatat    4140
aatcagtgta ttccaatatg tactacgatt tccaatgtct ttattgtcgc cgtatgcaat    4200
cggcgtcaca aaataatccc cggtgacttt ctttttaatcc aggatgaaat aatatgttat    4260
tataattttt gcgatttggt ccgttatagg aattgaagtg tgcttgcggt cgccaccact    4320
cccatttcat aattttacat gtatttgaaa aataaaaatt tatggtattc aatttaaaca    4380
cgtatacttg taaagaatga tatcttgaaa gaaatatagt ttaaatattt attgataaaa    4440
taacaagtca ggtattatag tccaagcaaa aacataaatt tattgatgca agtttaaatt    4500
cagaaatatt tcaataactg attatatcag ctggtacatt gccgtagatg aaagactgag    4560
```

-continued tgcgatatta tggtgtaata cata                                                    4584

<210> SEQ ID NO 13
<211> LENGTH: 22
<212> TYPE: DNA
<213> ORGANISM: artificial sequence
<220> FEATURE:
<223> OTHER INFORMATION: Primer sequence

<400> SEQUENCE: 13
gaggattagg gtttcaacgg ag                                                      22

<210> SEQ ID NO 14
<211> LENGTH: 21
<212> TYPE: DNA
<213> ORGANISM: Artificial Sequence
<220> FEATURE:
<223> OTHER INFORMATION: Primer Sequence

<400> SEQUENCE: 14
gagaattgag ctgagacgag g                                                       21

<210> SEQ ID NO 15
<211> LENGTH: 25
<212> TYPE: DNA
<213> ORGANISM: Artificial Sequence
<220> FEATURE:
<223> OTHER INFORMATION: Probe Sequence

<400> SEQUENCE: 15
agagaagttt cgacggattt cgggc                                                   25

<210> SEQ ID NO 16
<211> LENGTH: 29
<212> TYPE: DNA
<213> ORGANISM: Artificial Sequence
<220> FEATURE:
<223> OTHER INFORMATION: Primer Sequence

<400> SEQUENCE: 16
acaagagtgg attgatgatc tagagaggt                                               29

<210> SEQ ID NO 17
<211> LENGTH: 29
<212> TYPE: DNA
<213> ORGANISM: Artificial Sequence
<220> FEATURE:
<223> OTHER INFORMATION: Primer Sequence

<400> SEQUENCE: 17
ctttgatgcc tatgtgacac gtaaacagt                                               29

<210> SEQ ID NO 18
<211> LENGTH: 29
<212> TYPE: DNA
<213> ORGANISM: Artificial Sequence
<220> FEATURE:
<223> OTHER INFORMATION: Probe Sequence

<400> SEQUENCE: 18
agggtgttgt ggctggtatt gcttacgct                                               29

<210> SEQ ID NO 19
<211> LENGTH: 20
<212> TYPE: DNA
<213> ORGANISM: Artificial Sequence

```
<220> FEATURE:
<223> OTHER INFORMATION: Primer Sequence

<400> SEQUENCE: 19
cagagtccat gctcaccaat                                              20

<210> SEQ ID NO 20
<211> LENGTH: 19
<212> TYPE: DNA
<213> ORGANISM: Artificial Sequence
<220> FEATURE:
<223> OTHER INFORMATION: Primer Sequence

<400> SEQUENCE: 20
acgtggcaac ttgaaatcc                                               19

<210> SEQ ID NO 21
<211> LENGTH: 24
<212> TYPE: DNA
<213> ORGANISM: Artificial Sequence
<220> FEATURE:
<223> OTHER INFORMATION: Probe Sequence

<400> SEQUENCE: 21
tggagatgtg gttgtgtggg acaa                                         24

<210> SEQ ID NO 22
<211> LENGTH: 26
<212> TYPE: DNA
<213> ORGANISM: artificial sequence
<220> FEATURE:
<223> OTHER INFORMATION: Primer Sequence

<400> SEQUENCE: 22
acaagagtgg attgatgatc tagaga                                       26

<210> SEQ ID NO 23
<211> LENGTH: 26
<212> TYPE: DNA
<213> ORGANISM: Artificial Sequence
<220> FEATURE:
<223> OTHER INFORMATION: Primer Sequence

<400> SEQUENCE: 23
ctttgatgcc tatgtgacac gtaaac                                       26

<210> SEQ ID NO 24
<211> LENGTH: 29
<212> TYPE: DNA
<213> ORGANISM: Artificial Sequence
<220> FEATURE:
<223> OTHER INFORMATION: Probe Sequence

<400> SEQUENCE: 24
ccagcgtaag caataccagc cacaacacc                                    29

<210> SEQ ID NO 25
<211> LENGTH: 21
<212> TYPE: DNA
<213> ORGANISM: Artificial Sequence
<220> FEATURE:
<223> OTHER INFORMATION: Primer Sequence

<400> SEQUENCE: 25
cgccgaagta tcgactcaac t                                            21
```

<210> SEQ ID NO 26
<211> LENGTH: 19
<212> TYPE: DNA
<213> ORGANISM: Artificial Sequence
<220> FEATURE:
<223> OTHER INFORMATION: Primer Sequence

<400> SEQUENCE: 26
gcaacgtcgg ttcgagatg                                             19

<210> SEQ ID NO 27
<211> LENGTH: 24
<212> TYPE: DNA
<213> ORGANISM: Artificial Sequence
<220> FEATURE:
<223> OTHER INFORMATION: Probe Sequence

<400> SEQUENCE: 27
tcagaggtag ttggcgtcat cgag                                       24

<210> SEQ ID NO 28
<211> LENGTH: 1453
<212> TYPE: DNA
<213> ORGANISM: Glycine max

<400> SEQUENCE: 28
gcagatgaag ataaagaaaa tgaaaagata aactaaatta gtctagactt tcttggctaa    60
agtagagctt tagagtacaa attcaaacaa acttacatcc cccgaaagtc ttcaagtaag   120
ccgaagtgac ctattagctt cgttttttcat gcttccatga ttaaaaaagt aattgcagaa   180
ctccttccag tatatgagct cgaattgggg tgccagatat gctaattaat tacttttatg   240
atgcaggcaa gtgtgttttc agatgctgtt cgggatgatg ttgattttta taagtatgaa   300
ctgcactcct ttagctttga agtttgatca ctagtggata aattatttat atcttgagct   360
ttgaaaatct tccaatgaaa cttcattcac actttctgtg aaaatatca tctattaaag    420 aatcttgtcg tggtcaatgc tatgcatgac aacatattaa ctatttaaaa gataacttaa   480
aattataaat agttacatat tataaaatgc tgtggtggac atgttaccac ttgtagaatt   540
tatatagtaa aattgaatct ataacaacac gacactttat gtttatggaa ttgtcatgta   600
tgtgataata aataagatta tgaaattat tataaaaaac aaggccttaa tcgaaaattc     660
aatatctttc tatttttta ttttataata gtaatataat taaggtgctt tattttgttt    720
tctcttaatt accgtaattc tcatttaaat acaacttttc tagcttatga tattgaaagt   780
taattaaaaa accaataacg tcctgaattt taatctaaaa cttctagtac gtttggtttc   840
acattttaga tataatttt aaagttaat agttataaat ttgtatttta aatgtgattt     900
tttttctatt tttaatgact ttttaaccat gtacagttat tcatactgat ttttaaact    960 gtttgcttga agagaccgtt tttgacacca agttaaagag gtcattatct cttctaaaat  1020
cctaagatat aatttccaaa tgaaaccaaa tttgtaatgt agcgaagatg agctgccaca  1080
ttgtgttctt gaggtcgagg cactactagc cctgtgtttc tgtgtagttt tactagcaac  1140
acaagttttt tcttttttc aaaaataaaa agaaagaag aaaaaaaatg tgatgggtca    1200
ctcacgggtt tgcaatgtta gtgtagcatc agcccaatcc aaactatctt ccataccaat  1260
ttccaagttt taatttaaat ttaaatttct tgactctgtt ggacctgaat tgtgtggctt  1320
acattgaccc tctcgaaaac atctgaggaa gaagtctttg catccacgtg gcagaataag  1380
agccactata gcatgacaaa atatcagcat gagaatccac atccaaatcc acgaccaatg  1440

```
aggtgttgct gag                                                        1453

<210> SEQ ID NO 29
<211> LENGTH: 1454
<212> TYPE: DNA
<213> ORGANISM: Glycine max

<400> SEQUENCE: 29
agcagatgaa gataaagaaa atgaaaagat aaactaaatt agtctagact ttcttggcta      60
aagtagagct ttagagtaca aattcaaaca aacttacatc ccccgaaagt cttcaagtaa     120
gccgaagtga cctattagct tcgttttcca tgcttccatg attaaaaaag taattgcaga     180
actccttcca gtatatgagc tcgaattggg gtgccagata tgctaattaa ttactttat      240 gatgcaggca agtgtgtttt cagatgctgt tcgggatgat gttgatttt ataagtatga      300 actgcactcc tttagctttg aagtttgatc actagtggat aaattattta tatcttgagc     360
tttgaaaatc ttccaatgaa acttcattca cactttctgt gaaaaatatc atctattaaa     420
gaatcttgtc gtggtcaatg ctatgcatga aacatatta actatttaaa agataactta     480
aaattataaa tagttacata ttataaaatg ctgtggtgga catgttacca cttgtagaat     540
ttatatagta aaattgaatc tataacaaca cgacactta tgtttatgga attgtcatgt      600
atgtgataat aaataagatt aatgaaatta ttataaaaaa caaggcctta atcgaaaatt     660
caatatcttt ctattttttt attttataat agtaatataa ttaaggtgct ttattttgtt     720
ttctcttaat taccgtaatt ctcatttaaa tacaactttt ctagcttatg atattgaaag     780
ttaattaaaa aaccaataac gtcctgaatt ttaatctaaa acttctagta cgtttggttt     840
cacattttag atataatttt taaaagttaa tagtttataaa tttgtatttt aaatgtgatt     900
ttttttctat ttttaatgac ttttttaacca tgtacagtta ttcatactga ttttttaaac    960
tgtttgcttg aagagaccgt ttttgacacc aagttaaaga ggtcattatc tcttctaaaa    1020
tcctaagata taatttccaa atgaaaccaa atttgtaatg tagcgaagat gagctgccac    1080
attgtgttct tgaggtcgag gcactactag ccctgtgttt ctgtgtagtt ttactagcaa    1140
cacaagtttt ttcttttttt caaaaataaa aagaaagaa gaaaaaaaat gtgatgggtc    1200
actcacgggt ttgcaatgtt agtgtagcat cagcccaatc caaactatct tccataccaa    1260
tttccaagtt ttaatttaaa tttaaatttc ttgactctgt tggacctgaa ttgtgtggct    1320
tacattgacc ctctcgaaaa catctgagga agaagtcttt gcatccacgt ggcagaataa    1380
gagccactat agcatgacaa aatatcagca tgagaatcca catccaaatc cacgaccaat    1440
gaggtgttgc tgag                                                      1454
```